(12) United States Patent
Sambandan et al.

(10) Patent No.: US 10,379,095 B2
(45) Date of Patent: *Aug. 13, 2019

(54) GAS SENSOR ELEMENT

(71) Applicant: NITTO DENKO CORPORATION, Osaka (JP)

(72) Inventors: Ekambaram Sambandan, Carlsbad, CA (US); Jie Cai, Oceanside, CA (US); Hiroyuki Katayama, Osaka (JP)

(73) Assignee: Nitto Denko Corporation, Osaka (JP)

( * ) Notice: Subject to any disclaimer, the term of this patent is extended or adjusted under 35 U.S.C. 154(b) by 272 days.

This patent is subject to a terminal disclaimer.

(21) Appl. No.: 15/360,790

(22) Filed: Nov. 23, 2016

(65) Prior Publication Data

US 2017/0146504 A1 May 25, 2017

Related U.S. Application Data

(60) Provisional application No. 62/260,132, filed on Nov. 25, 2015.

(51) Int. Cl.
G01N 27/00 (2006.01)
G01N 33/00 (2006.01)
A61B 5/08 (2006.01)
G01N 27/12 (2006.01)

(52) U.S. Cl.
CPC ......... *G01N 33/0047* (2013.01); *A61B 5/082* (2013.01); *G01N 27/125* (2013.01)

(58) Field of Classification Search
CPC ............. G01N 27/125; G01N 33/0047; G01N 33/497; G01N 33/0031; G01N 33/0036; G01N 2033/4975; G01N 2800/042; A61B 5/082

See application file for complete search history.

(56) References Cited

U.S. PATENT DOCUMENTS 9,739,738 B2 * 8/2017 Sambandan ............ H01L 29/04
9,933,382 B2 * 4/2018 Sambandan ............ H01L 29/04
2009/0148347 A1 * 6/2009 Lee ...................... C04B 35/4682
422/83

* cited by examiner

Primary Examiner — Blake A Tankersley
(74) Attorney, Agent, or Firm — K&L Gates LLP; Louis C. Cullman; Hal Gibson

(57) ABSTRACT

Described herein are devices for detecting the concentration of acetone gas. Some gas sensor devices comprise: a gas sensor element that includes a boron-doped the polycrystalline n-type semiconductor epsilon $WO_3$. In addition, multi-detector gas sensor elements are also described including at least one based on the aforementioned gas sensor element where the other elements differ in material properties. In addition, methods for detecting acetone gas based on the disclosed elements are also described.

12 Claims, 12 Drawing Sheets

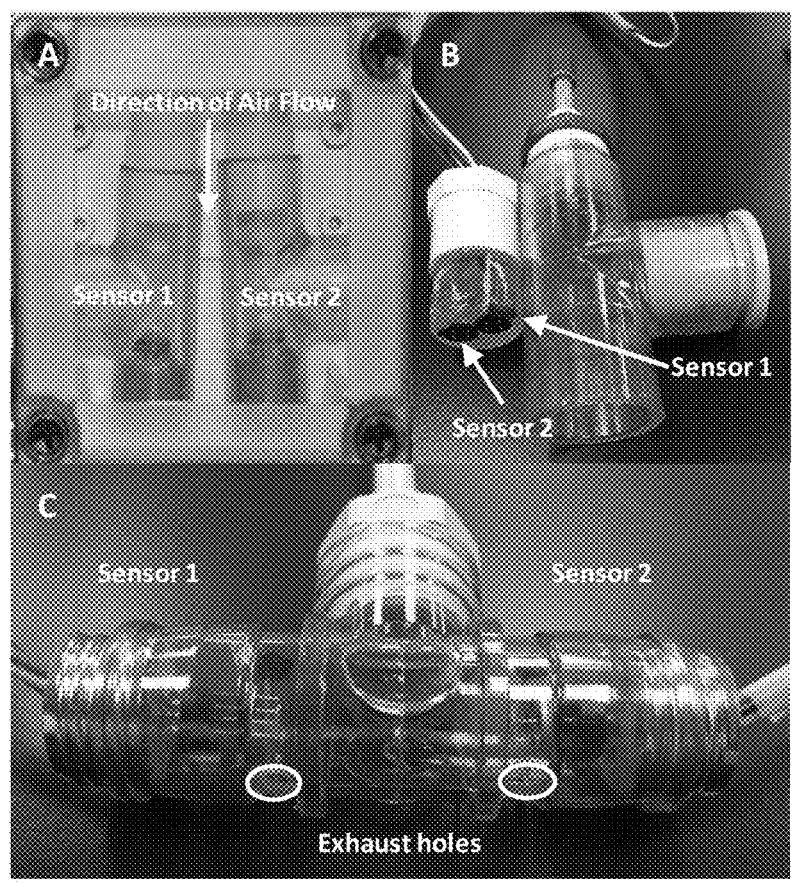
FIG. 12 Multiple Embodiments of a Dual Sensor Element
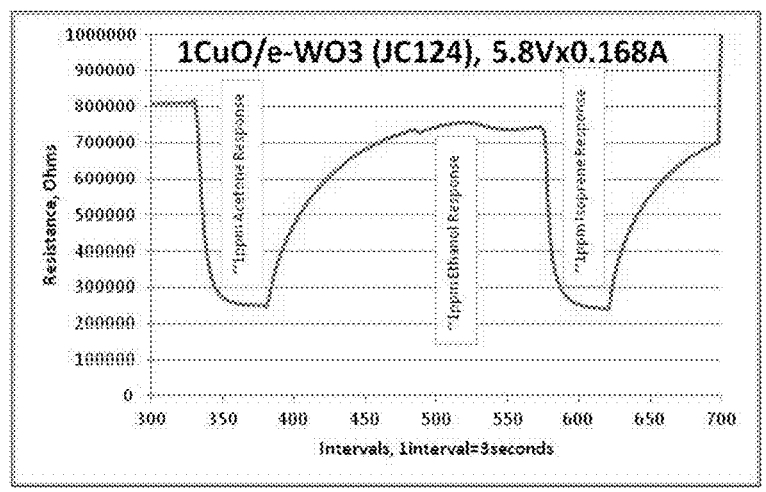
FIG. 13

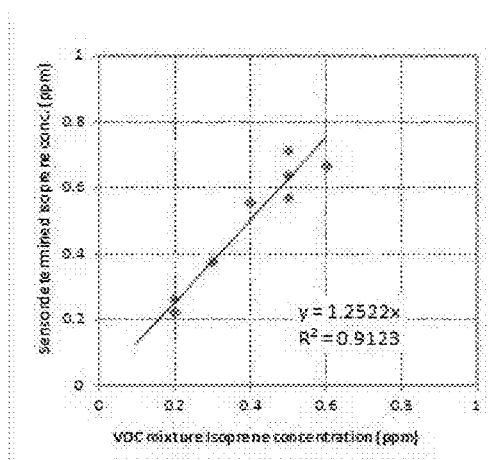
FIG. 21
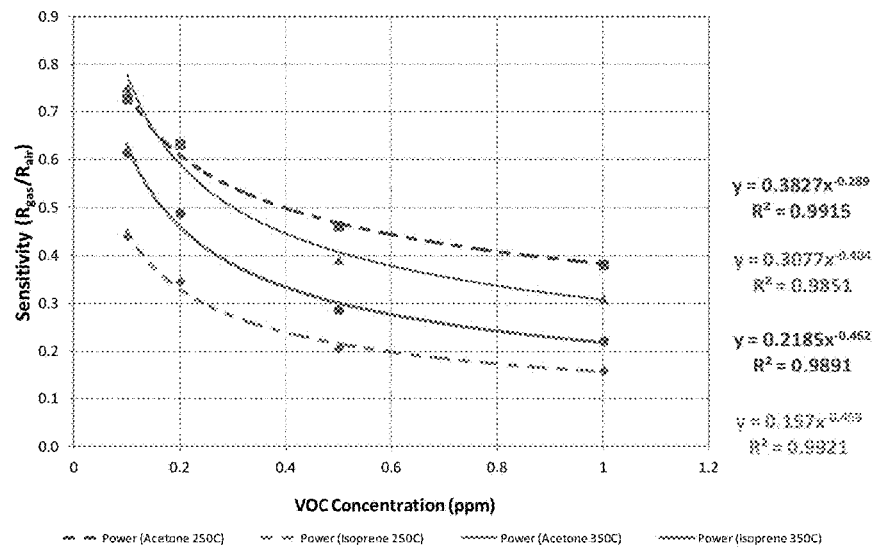
FIG. 22 Dual Sensor Element (both B-doped at two different T's) Characterization

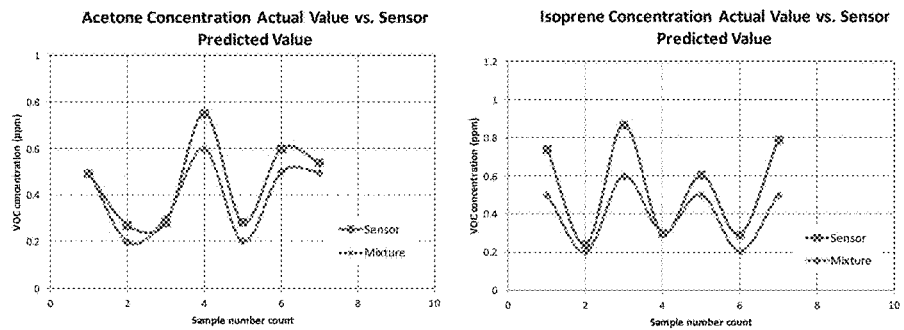
FIG. 23 Concentration Prediction Using Dual Sensor (both B doped at two T's)
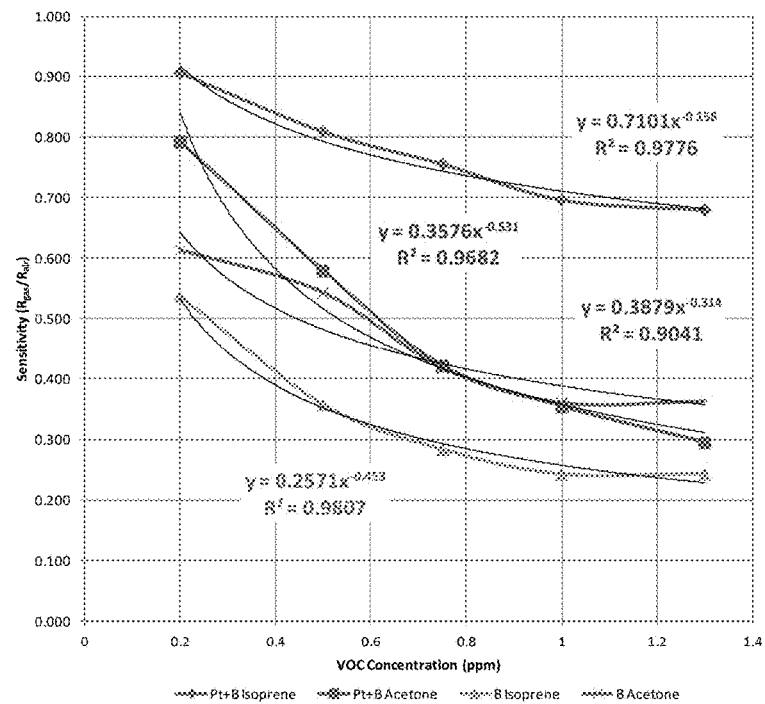
FIG. 24 Dual Sensor Element (B-doped & B+Pt Doped) Characterization

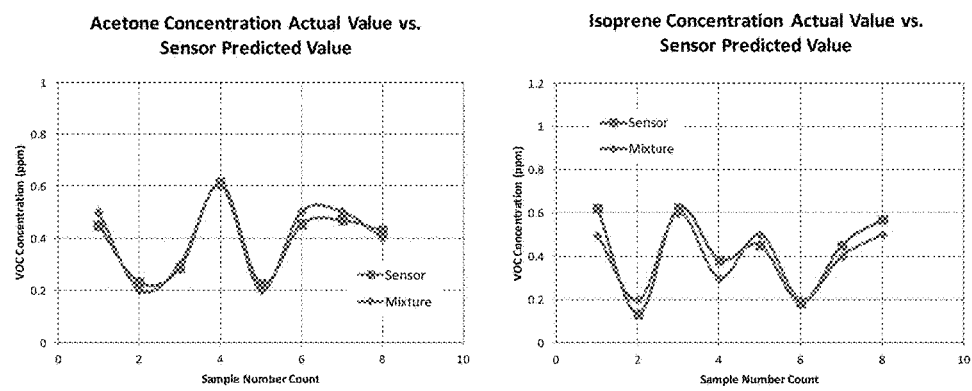
FIG. 25 Concentration Prediction Using Dual Sensor (B doped & B+Pt doped)

GAS SENSOR ELEMENT

The present application claims the benefit of U.S. Provisional Patent Application 62/260,132 filed Nov. 25, 2015, the entire contents of which is incorporated by reference herein.

BACKGROUND

Field

Some embodiments are related to a metal oxide material useful in breath gas analysis. Some embodiments are related to medical devices which analyze human breath to determine health conditions. Some embodiments are related to methods of detecting acetone to determine the presence of health conditions, such as diabetes.

Description of the Related Art

Scientists have discovered connections between certain illnesses and physical conditions that are associated with the presence of certain gases in mammalian expiratory breaths. Some scientists have even linked the detection of acetone in human breath to illness such as diabetes. M. Righettoni & A. Tricoli, *Toward Portable Breath Acetone Analysis for Diabetes Detection,* 5(3) J. Breath Res. (2011). To that end, gas sensing devices have been reported. United States Patent Publication 2009/0054799 (Pub. 26 Feb. 2009), United States Patent Publication 2010/0077840 (Pub. 1 Apr. 2010), United States Patent Publication 2013/0115706 (Pub. 9 May 2013).

In the art of gas sensors, tungsten oxide is one of the materials that can be used in gas sensors. Tungsten Oxide ($WO_3$) crystals can be formed by corner and edge sharing of $WO_6$ octahedra. Various phases can be obtained by corner sharing, e.g., monoclinic II (epsilon [$\epsilon$]-phase); triclinic (delta [$\delta$]-phase), monoclinic I (gamma [$\gamma$]-phase), orthorhombic (beta [$\beta$]-phase), tetragonal (alpha [$\alpha$]-phase), and cubic $WO_3$. The monoclinic II phase has been reported as generally stable only at subzero temperatures, with monoclinic I as the most stable phase at room temperature. H. Zheng, et al., *Nanostructured Tungsten Oxide—Properties, Synthesis, and Applications,* 21 Adv. Funct. Mater. 2175-2196 (2011). E-phase tungsten oxide has been described as useful for gas sensors. M. Righettoni & A. Tricoli, supra. While scientists have explored doping of tungsten oxide to improve its performance, doping has only used noble metals, Si, V, Cr, Cu, CuO, and VPO, see U.S. Pat. No. 8,980,640 (17 Mar. 2015); I. Jiménez, $NH_3$ *Interaction with Catalytically Modified Nano-$WO_3$ Powders for Gas Sensing Applications,* 150(4) J. Electrochem. Soc. H72-H80 (2003); L. Wang at al., *Ferroelectric $WO_3$ Nanoparticles for Acetone Selective Detection,* 20 Chem. Mater. 4794-4796 (2008); M. Righettoni et al., *Breath Acetone Monitoring by Portable Si:$WO_3$ Gas Sensors,* 738 Anal Chim Acta 69-75 (13 Aug. 2012); S. Kanan, et al., *Semiconducting Metal Oxide Based Sensors for Selective Gas Pollutant Detection,* 9 Sensors 8159, 8162 (2009); A. Rydosz et al., *Deposition of Nanocrystalline WO3 and CuO Thin Film in View of a Gas Sensor Applications,* Society of Digital Information and Wireless Communications (SDIWC): The Second International Conference on Technological Advances in Electrical, Electronics and Computer Engineering (TAEECE2014) Proceedings 150-55 (March 2014).

Even with advances, metal oxide gas detectors still require the use of heaters to meet operating temperature requirements. M. Righettoni & A. Tricoli, supra. Silicon-doped epsilon-phase ($\epsilon$ or Epsilon) $WO_3$ is a nano metal oxide acetone sensing material, but it is described as working from about 300° C. to about 400° C., a potentially difficult temperature to attain in a portable device without the addition of a heater. M. Righettoni et al., supra. In addition, operating temperatures near 400° C. or above can have adverse effects upon the sensing material, e.g., changing the phase of some of the material.

Despite advances, there is still a need for an acetone sensor that provides efficient gas detection for use in portable devices that could be used for diagnosis and self-monitoring of outpatients having various physical conditions, including diabetes.

SUMMARY

In some embodiments, a gas sensor element is described, comprising at least a first sensor, the first sensor comprising a first electrode and a second electrode, wherein the first electrode and the second electrode are separated by a gap of about 1 mil to about 10 mils, and a polycrystalline n-type semiconductor material, wherein the polycrystalline n-type semiconductor material comprises boron-doped $WO_3$, wherein the n-type semiconductor is also optionally doped or loaded with V, Sm, or combinations thereof, and is in physical contact with both the first and second electrodes. In some embodiments, the polycrystalline n-type semiconductor is also doped or loaded with V, Sm, CuO, or combinations thereof instead of being doped or loaded with V, Sm, or combinations thereof. In some embodiments, the polycrystalline n-type semiconductor material is also doped or loaded with a noble metal. In some embodiments, the noble metal is any combination of palladium, gold, or platinum. In some embodiments, the polycrystalline n-type semiconductor material is also doped with Ti, Ce, or combinations thereof. In some embodiments, the $WO_3$ is epsilon-phase $WO_3$.

In some embodiments, the aforementioned gas sensor element is described, also comprising a second sensor, the second sensor comprising a first electrode and a second electrode, wherein the first electrode and the second electrode are separated by a gap of about 1 mil to about 10 mils, and a polycrystalline n-type semiconductor material in physical contact with both the first and second electrodes, where the polycrystalline n-type semiconductor material comprises boron-doped $WO_3$. In some embodiments, the polycrystalline n-type semiconductor material is also doped or loaded with any combination of V, Sm, CuO or combinations thereof. In some embodiments, the polycrystalline n-type semiconductor material is also doped or loaded with a noble metal. In some embodiments, the noble metal is any combination of palladium, gold, or platinum. In some embodiments, the polycrystalline n-type semiconductor material is also doped with Ti, Ce, or combinations thereof. In some embodiments, the $WO_3$ is epsilon-phase $WO_3$.

In some embodiments, a method for testing for the presence of acetone is described, comprising: (1) testing a gas sample at 350° C. with a first sensor, wherein the first sensor comprises a first electrode and a second electrode, wherein the first electrode and the second electrode are separated by a gap of about 1 mil to about 10 mils, and a polycrystalline n-type semiconductor material comprises $WO_3$, the semiconductor material physically contacting both the first and second electrodes, where the polycrystalline n-type semiconductor material is doped with Boron; (2) testing the same gas sample at 250° C. with a second sensor, wherein the second sensor comprises a first electrode and a second electrode, wherein the first electrode and the second electrode are separated by a gap of about 1 mil to about 10 mils, and a polycrystalline n-type semiconductor material comprises $WO_3$, the semiconductor material physically contacting both the first and second electrodes, where the polycrystalline n-type semiconductor material is doped or loaded with any combination of Ti, Ce, V, Sm, CuO, or a noble metal; and (3) comparing the results of the first and second sensors to arrive at a determination of the amounts of a first gas and a second gas, where one gas is acetone. In some embodiments, the second sensor's polycrystalline n-type semiconductor material is also doped with Boron. In some embodiments, the first sensor's polycrystalline n-type semiconductor material can be doped or loaded with any combination of Ti, Ce, V, Sm, CuO, or a noble metal. In some embodiments, the noble metal is any combination of palladium, gold, or platinum. In some embodiments, the $WO_3$ is epsilon-phase $WO_3$. In some embodiments, the two gases detected by the method are acetone and isoprene.

In some embodiments, another method for testing for the presence of acetone is described, comprising: (1) testing a gas sample at 350° C. with a first sensor, wherein the first sensor comprises a first electrode and a second electrode, wherein the first electrode and the second electrode are separated by a gap of about 1 mil to about 10 mils and a polycrystalline n-type semiconductor material comprises $WO_3$, the semiconductor material physically contacting both the first and second electrodes, where the polycrystalline n-type semiconductor material is doped with Boron; (2) testing the same gas sample at 350° C. with a second sensor, wherein the second sensor comprises a first electrode and a second electrode, wherein the first electrode and the second electrode are separated by a gap of about 1 mil to about 10 mils, and a polycrystalline n-type semiconductor material comprises $WO_3$, the semiconductor material physically contacting both the first and second electrodes, where the polycrystalline n-type semiconductor material is doped or loaded with any combination of Ti, Ce, V, Sm, CuO, or a noble metal such that the material properties between the first sensor and the second sensor differ; and (3) comparing the results of the first and second sensors to arrive at a determination of the amounts of a first gas and a second gas, where one gas is acetone. In some embodiments, the second sensor's polycrystalline n-type semiconductor material is also doped with Boron. In some embodiments, the first sensor's polycrystalline n-type semiconductor material can be doped or loaded with any combination of Ti, Ce, V, Sm, CuO, or a noble metal. In some embodiments, the noble metal is any combination of palladium, gold, or platinum. In some embodiments, the $WO_3$ is epsilon-phase $WO_3$. In some embodiments, of the two gases detected by the method are acetone and isoprene.

These and other embodiments are described in greater detail below.

BRIEF DESCRIPTION OF THE DRAWINGS

FIG. 12 is a photograph of testing several embodiments of the device described herein.

FIG. 13 is a graph depicting the SE-2 sensor sensitivity at 350° C. as described in Example 25.

FIG. 21 is a graph depicting the sensor determined isoprene concentration as described in Example 27 (using SE-1 and SE-3 dual sensor system).

FIG. 22 is a graph showing the sensitivity responses for a dual sensor system where both sensors are boron-doped $\varepsilon$-$WO_3$ where one sensor is at 350° C. and the other is at 250° C. as well as curve-fitted relationships to predict concentration from resistivity.

FIG. 23 consists of two plots for Example 29, Dual Sensor #1: (left) a comparison of the prediction of the concentration of acetone for various measured samples; and (right) a comparison of the prediction of concentration of isoprene for various measured samples.

FIG. 24 is a graph showing the sensitivity responses for a dual sensor system where one sensor is a boron-doped $\varepsilon$-$WO_3$ sensor and one is a Pt-doped, boron-doped $\varepsilon$-$WO_3$ where both sensors are at 350° C. as well as curve-fitted relationships to predict concentration from resistivity.

FIG. 25 consists of two plots for Example 30, Dual Sensor #2: (left) a comparison of the prediction of concentration of acetone for various samples; and (right) a comparison of the sensor prediction of concentration of isoprene for various samples.

DETAILED DESCRIPTION

Figure 1:
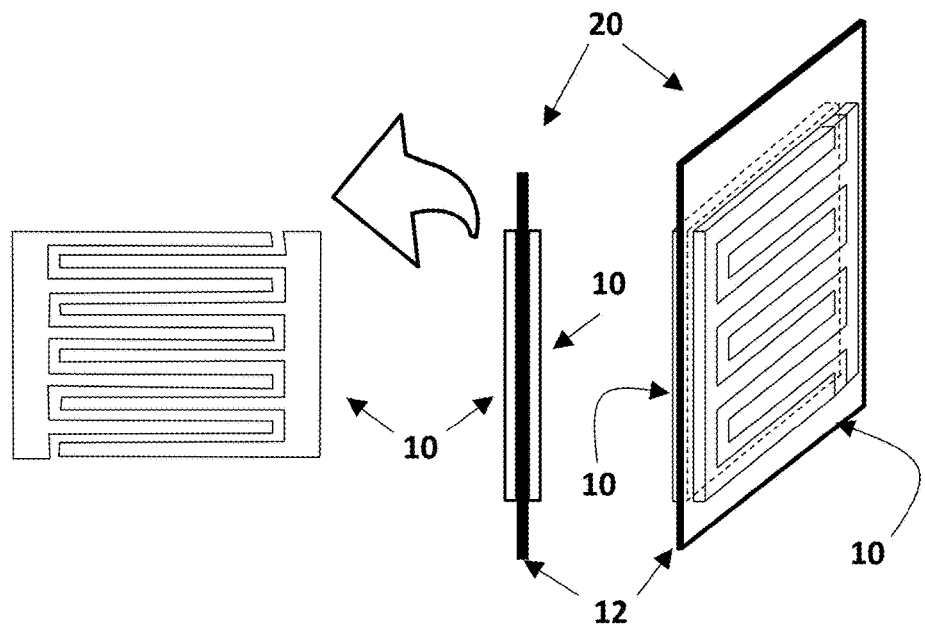
FIG. 1 is a depiction of a perspective view of some embodiments of the devices described herein.

The term "polycrystalline material" refers to any material comprising a plurality of grains (i.e., crystals) of the material, including grains or crystals that are bonded directly together by inter-granular bonds. The crystal structures of the individual grains of the material may be randomly oriented in space within the polycrystalline material.

As used herein, the term "epsilon phase" has the ordinary meaning known to a person of ordinary skill in the art.

As used herein, the term "doped" refers to elements that are incorporated into the crystal lattice of the compound, for example as substituted within defined positions within the crystal lattice or otherwise interstitially included within the crystal.

The term "loaded" refers to the non-valent combination, e.g., a physical mixture and/or adjacent disposition of a first material, e.g., the n-type semiconductor material, and a second material, e.g., with co-catalytic materials such as CuO.

The term 'n-type semiconductor" has the ordinary meaning known to a person of ordinary skill in the art.

The current disclosure describes gas sensor elements and methods for sensing using a boron-doped epsilon-phase $WO_3$ as a gas sensor material. Some embodiments describe a gas sensor element, the gas sensor element comprising at least a first sensor, the first sensor comprising a first electrode and a second electrode, wherein the first electrode and the second electrode are separated by a gap of about 1 mil to about 10 mils, and an n-type semiconductor material, wherein the semiconductor material is in physical contact with both the first and second electrodes.

In some embodiments, the n-type semiconductor material can be polycrystalline. In some embodiments, the n-type semiconductor has an absorption edge of at least 600 nm, at least 550 nm, at least 500 nm, at least 475 nm, and/or at least 450 nm. In some embodiments, the n-type semiconductor material can have an octahedral lattice. In some embodiments, the n-type semiconductor material can be a monoclinic phase material. In some embodiments, the n-type semiconductor material can be a monoclinic I phase material. In some embodiments, the n-type semiconductor material can be a monoclinic II phase material. In some embodiments, the n-type semiconductor material can have a spontaneous dipole moment. In some embodiments, the n-type semiconductor material can be $WO_3$. Tungsten Oxide ($WO_3$) crystals can be formed by corner and edge sharing of $WO_6$ octahedra. Various phases can be obtained by corner sharing, e.g., monoclinic II (epsilon [ε]-phase); triclinic (delta [δ]-phase), monoclinic I (gamma [γ]-phase), orthorhombic (beta [β]-phase), tetragonal (alpha [α]-phase), and cubic $WO_3$. While not wanting to be limited by theory, while monoclinic II phase may be stable only at subzero temperatures and monoclinic I phase appears to be the most stable phase at room temperature, the monoclinic II phase (ε-phase) is useful for gas sensors. In some embodiments, the $WO_3$ can be epsilon-phase $WO_3$ (ε-$WO_3$). In some embodiments, the $WO_3$ can be gamma-phase $WO_3$ (γ-$WO_3$). In some embodiments, the n-type semiconductor can be epsilon-phase tungsten oxide, gamma-phase tungsten oxide, and/or mixtures thereof. Comparison of an x-ray diffraction (XRD) pattern of a given standard and the produced sample is one of several methods that may be used to determine whether the sample comprises a particular phase. Exemplary standards include those XRD spectra provided by the National Institute of Standards and Technology (NIST) (Gaithersburg, Md., USA) and/or the International Centre for Diffraction Data (ICDD, formerly the Joint Committee on Powder Diffraction Standards [JCPDS]) (Newtown Square, Pa., USA). In some embodiments, a gas sensor is described as above, wherein the polycrystalline n-type material can be $WO_3$. In some embodiments, a gas sensor is described, wherein the $WO_3$ can be epsilon phase $WO_3$. While not wanting to be bound by theory, it is believed that the spontaneous dipole of the ε-$WO_3$ may be related to the material lattice so that changes in the lattice may change the strength of the dipoles (in other words, a change in the spontaneous polarization). It is believed that a change in the spontaneous dipole moment can result in a change in the surface charge of the material.

In some embodiments, the n-type semiconductor material comprises primary particles having a median diameter of about 0.2 μm to about 1.1 μm, and/or about 0.3 μm to about 1.0 μm. In one embodiment, the median diameter can be between about 0.4 μm to about 0.8 μm and/or any combination of the described limitation. In some embodiments, the median diameter can be about 0.4 μm to about 0.5 μm, e.g., about 0.50086 μm.

In some embodiments, the dipole moment of the n-type semiconductor can be modified by changing the semiconductor crystal lattice. In some embodiments the crystal lattice is modified by doping the semiconductor. In some embodiments, the n-type semiconductor can be doped with at least one naturally occurring element e.g. Group III acceptor element like boron, B. In some embodiments, the Group III acceptor element can be B. In some embodiments, the dopant can be B. In some embodiments, the dopant can be $B^{3+}$. In some embodiments, the n-type semiconductor comprises boron-doped $WO_3$. As described above, in some embodiments, the dopant concentration, such as a B dopant, can be between a lower limit of 0.0001 wt %, 0.01 wt %, 0.05 wt %, 0.10 wt %, 0.15 wt % ratio to an upper limit of about 0.2 wt %, 0.25 wt %, 0.4 wt %, 0.5 wt %, 0.75 wt %, 1.0 wt % ratio and/or any combination of the described limits. In some embodiments, the wt % ratio can be about 0.190 gm (B)/100 gm (semiconductor), e.g., about 0.19 wt % ratio. While not wanting to be limited by theory, it is believed that if the dopant concentration is above a threshold amount, the amount of ε-$WO_3$ and/or boron present can be insufficient to provide the desired lower temperature phase stability. In addition, while not wanting to be limited by theory, it is believed that if x and/or the dopant concentration is below a first threshold amount, the amount of ε-$WO_3$ and/or boron present can also be insufficient to provide the desired room temperature phase stability. While not wanting to be limited by theory, it is also believed that if the dopant concentration is below a second threshold amount, the dopant can segregate out instead of doping into the lattice.

In some embodiments, the n-type semiconductor can also comprise a co-catalyst. In some embodiments, the polycrystalline n-type semiconductor is loaded with the co-catalyst. In other embodiments, the polycrystalline n-type semiconductor is doped with the co-catalyst. In some embodiments, the polycrystalline n-type semiconductor can comprise a combination of doped and/or loaded co-catalyst. In some embodiments, the co-catalyst can be inorganic. In some embodiments, the inorganic co-catalyst can be a binder. In some embodiments, the co-catalyst can comprise an oxide, such as a metal oxide. In some embodiments, the co-catalyst can comprise a metal oxide, including any metal oxide based on oxides of Ce, Co, Cr, Cu, Fe, Mn, Ni, Sn, Ti, V, and Zr. In some embodiments, the co-catalyst can comprise CuO, $CeO_2$, MnOx, $CuCr_2O_4$, $Co_3O_4$, $MoO_3$, NiO, $Fe_2O_3$, $SnO_2$, $Sm_2O_3$, $TiO_2$, $VC_2O_5$, $ZrO_2$ or the like. In some embodiments, the co-catalyst can comprise a composite material that further comprises of a physical mixture of an inorganic co-catalyst and a semiconductor material. In another embodiment, the ratio of the n-type semiconductor material to co-catalyst, e.g., CuO, can be between a lower limit of 0.0001 wt %, 0.01 wt %, 0.05 wt %, 0.10 wt %, 0.5 wt %, 0.8 wt %, 0.9 wt % ratio to an upper limit of about 1.1%, 1.2%, 1.5%, 2.0 wt %, 5.0 wt %, 7.5 wt %, and/or 10.0 wt % ratio and/or any combination of the described limits. In some embodiments, the co-catalyst can comprise CuO. In some embodiments, the wt % ratio can be about, 1 wt %, or 1 gm of CuO to about 100 gm of $WO_3$.

In some embodiments, the n-type semiconductor can be loaded with at least one metal, metal oxide, and/or metal hydroxide. In other embodiments, the polycrystalline n-type semiconductor is doped with at least one metal, metal oxide, and/or metal hydroxide. In some embodiments, the polycrystalline n-type semiconductor can comprise a combination of doped and/or loaded metal, metal oxides, and/or metal hydroxides. In some embodiments, the metal, metal oxide, and/or metal hydroxide can be selected from those containing noble metals. In some embodiments, the doped and/or loaded metal, metal oxide, and/or metal hydroxide can be selected from at least one noble metal. In some embodiments, the noble metals can be selected from Au, Ag, Pt, Pd, Ir, Ru, Rh or one or more of their oxides and/or hydroxides. In some embodiments, the noble metal can comprise any combination of palladium, gold and/or platinum. In some embodiments, the doped and/or loaded element is selected from transition metals, their oxides and/or hydroxides. In other embodiments, the metal, metal oxide, and/or metal hydroxide may be chosen from different groups of elements including at least one transition metal and at least one noble metal or one or more of their respective oxides and hydroxides. In some embodiments, the metal, metal oxide, and/or metal hydroxide can comprise any combination of Ti, Ce, V, Sm, Si, Pt, Au, and/or Pd. In some embodiments, the doped and/or loaded element can be Pt or one or more of its oxides and/or hydroxides. In some embodiments, Pt or an oxide or hydroxide thereof, is present in an amount of about 0.005-5 wt %, about 0.005-0.02 wt %, about 0.01-0.05 wt %, about 0.04-0.1 wt %, about 0.1-0.5 wt %, about 0.5-1 wt %, about 1-2 wt %, or any amount in a range bounded by any of these values. In some embodiments, the doped and/or loaded element can be V or one or more of its oxides and/or hydroxides. In some embodiments, V or an oxide or hydroxide thereof, is present in an amount of about 0.005-5 wt %, about 0.005-0.02 wt %, about 0.15-0.25 wt %, about 0.01-0.05 wt %, about 0.04-0.1 wt %, or any amount in a range bounded by any of these values. In some embodiments, the doped and/or loaded element can be Sm or one or more of its oxides and/or hydroxides. In some embodiments, Sm or an oxide or hydroxide thereof, is present in an amount of about 0.005-5 wt %, about 0.005-0.02 wt %, about 0.15-0.25 wt %, about 0.01-0.05 wt %, about 0.04-0.1 wt %, or any amount in a range bounded by any of these values. In some embodiments, the doped element can be Ti. In some embodiments, the doped element can be Ce. Loaded elements can be provided by post synthesis methodologies like impregnation (Liu, M., Qiu, X., Miyauchi, M., and Hashimoto, K., Cu(II) Oxide Amorphous Nanoclusters Grafted $Ti^{3+}$ Self-Doped $TiO_2$: An Efficient Visible Light Photocatalyst. Chemistry of Materials, published online 2011), photoreduction (Abe et al., Journal of the American Chemical Society, 130(25): 7780-7781, 2008), and sputtering. In some embodiments, the loading may be carried out by electrostatic adsorption. As a preferred embodiment, loading metals on semiconductors may be carried out as described in US Patent Publication Number US2008/0241542 which is incorporated by reference herein in its entirety.

In some embodiments, the gas sensor element can detect the presence of constituent gases within a range of temperatures. In some embodiments, the sensor element can detect the presence of constituent gases between 0° C. and 400° C. In some embodiments, the sensor element can detect the presence of constituent gases between 0° C. and 200° C., 100° C. and 300° C., or 200° C. and 400° C. In some embodiments, the sensor element can detect the presence of constituent gases between 0° C. and 20° C. In some embodiments, the sensor element can detect the presence of constituent gasses between 20° C. and 40° C. In some embodiments, the sensor element can detect the presence of constituent gases between 40° C. and 60° C. In some embodiments, the sensor element can detect the presence of constituent gases between 60° C. and 80° C. In some embodiments, the sensor element can detect the presence of constituent gasses between 80° C. and 100° C. In some embodiments, the sensor element can detect the presence of constituent gases between 100° C. and 120° C. In some embodiments, the sensor element can detect the presence of constituent gases between 120° C. and 140° C. In some embodiments, the sensor element can detect the presence of constituent gases between 140° C. and 160° C. In some embodiments, the acetone sensor element can detect the presence of constituent gases between 160° C. and 180° C. In some embodiments, the sensor element can detect the presence of constituent gases between 180° C. and 200° C. In some embodiments, the sensor element can detect the presence of constituent gases between 200° C. and 220° C. In some embodiments, the acetone sensor element can detect the presence of constituent gasses between 220° C. and 240° C. In some embodiments, the sensor element can detect the presence of constituent gases between 240° C. and 260° C. In some embodiments, the sensor element can detect the presence of constituent gases between 260° C. and 280° C. In some embodiments, the sensor element can detect the presence of constituent gases between 280° C. and 300° C. In some embodiments, the sensor element can detect the presence of constituent gases between 300° C. and 320° C. In some embodiments, the sensor element can detect the presence of constituent gases between 320° C. and 340° C. In some embodiments, the sensor element can detect the presence of constituent gases between 340° C. and 360° C. In some embodiments, the sensor element can detect the presence of constituent gases between 360° C. and 380° C. In some embodiments, the sensor element can detect the presence of constituent gases between 380° C. and 400° C. In some embodiment, the sensor can detect the presence of constituent gases at some or any combination of the above described temperatures. In some embodiments, the sensor element can detect the presence of constituent gases at room temperature. In other embodiments, the sensor element can detect the presence of constituent gases at temperatures between about 250° C. and about 350° C.

In some embodiments, the sensor element can detect the presence of constituent gases in presence of visible light. In some embodiments, the visible light can have a peak wavelength of between about 350 nm, about 375 nm, about 400 to about 500 nm, about 550 nm, about 600 nm, and/or about 650 nm, or a range of any combination of the aforedescribed wavelengths. In some embodiments, the sensor element can detect the presence of constituent gases in presence of an LED emitting at about the above described wavelengths, e.g., a Blue LED, e.g., about 455 nm, of power about 30-40 mW/cm$^2$ power. In some embodiments, the sensor can detect the presence of constituent gases at room temperature in the presence of the above described visible light. While not wanting to be limited by theory, it is believed that resistivity usually decreases at a higher temperature sensor operation when exposed to acetone. In some embodiments, the operation of a sensor could exhibit increased changes in resistivity upon exposure to acetone under Blue LED light.

In some embodiments, the constituent gases can comprise gases present in mammalian breath. In some embodiments, the constituent gas can comprise acetone. In some embodiments, the constituent gas can comprise isoprene. In other embodiments, the constituent gases can comprise some combination of acetone and isoprene.

In some embodiments, the aforedescribed gas sensor element comprises multiple sensors. In some embodiments, the aforementioned gas sensor element comprises at least two sensors. In some embodiments, a first sensor can be the aforedescribed gas sensor element; doped with boron. In some embodiments, the second sensor to the nth sensor, where n is the total number of sensors, defines a plurality of sensors. In some embodiments, each sensor in the plurality of sensors comprises a first electrode and a second electrode, wherein the first electrode and the second electrode are separated by a gap of about 1 mil to about 10 mils, and a polycrystalline n-type semiconductor material, wherein the semiconductor material is in physical contact with both the first and second electrodes. In some embodiments, the plurality of sensors can comprise embodiment(s) of the first gas sensor with the exception that for each of the plurality of sensors boron-doping is optional. In some embodiments, the plurality of sensors can comprise unique embodiments of the aforementioned first gas sensor such that each sensor in the gas sensor element has distinct material properties (i.e.: doping concentration, co-catalyst species, co-catalyst concentrations, loading species, and loading concentrations). While not wanting to be limited by theory, it is believed that sensors with different material properties can have differing reactions to the presence of different gas species which through analysis will enhance the detection of a specific gas species in a gas mixture. In some embodiments, the gas sensor element can comprise two sensors: a first sensor and a second sensor. In some embodiments, at least one sensor comprises boron-doped $WO_3$. In some embodiments, the second sensor can comprise $WO_3$ doped and/or loaded with Ti, Ce, V, Sm, CuO, and/or a noble metal such that the second sensor has distinct material properties from those of the first sensor. In some embodiments, the doped and/or loaded noble metal can comprise any combination of palladium, gold, and/or platinum. In some embodiments, the second sensor comprises polycrystalline n-type semiconductor doped with boron.

FIG. 1 depicts an embodiment of a gas sensor element 10. In addition, FIG also depicts an embodiment of a compound gas sensor element, 20. In some embodiments, the compound gas sensor element can comprise multiple gas sensor elements. In some embodiments, the compound gas sensor element is configured such that the gas sensor elements, 10, are back to back on the same substrate 12 and are exposed to the same atmosphere. In some embodiments, the gas sensor elements, 10, are of different materials such that they have different reactions to different gases.

Figure 2:
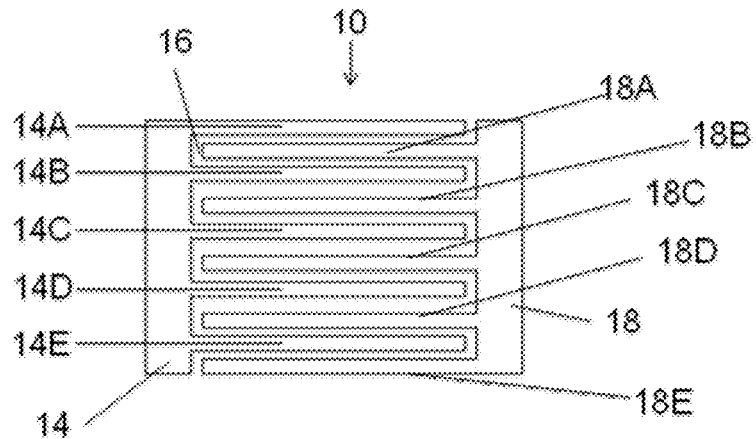
FIG. 2 is a plan view of some embodiments of a device described herein.

As depicted in FIG. 2, in some embodiments, the sensor element 10 can comprise a first electrode 14 and a second electrode 18. In some embodiments, the sensor can comprise an n-type semiconductor material 16 disposed between the first and second electrodes. In some embodiments, the n-type semiconductor material can be electrically connecting the first and second electrodes. In some embodiments, the n-type semiconductor material can be disposed between and/or physically contacting both the first and second electrodes. In some embodiments, the first electrode 14 can comprise at least one or a plurality of electrode fingers 14A, 14B, 14C, 14D, 14E, disposed over a substrate 12 (see FIG. 1). In some embodiments, the second electrode 18 can also comprise at least one or a plurality of electrode fingers 18A, 18B, 18C, 18D and 18E. In some embodiments, the respective electrode fingers are interdigitated. In some embodiments, at least one finger is sufficiently close to enable closing an electrical circuit across the gap through the semiconducting material. In some embodiments, at least 1 at least 2, at least 3, at least 4, or at least 5 electrode fingers can be interdigitated fingers. In some embodiments, the smallest gap between the first electrode 14 and the second electrode 18 defines a distance between the electrodes. In some embodiments, the distance between the electrodes can be between 0.01 mils to about 100 mils, between about 0.1 mils to about 25 mils, and/or between about 0.5 mils to about 10 mils, In some embodiments, an electrode of the device can comprise a plurality of interdigitated fingers, e.g., 14A-14E.

Figure 3:
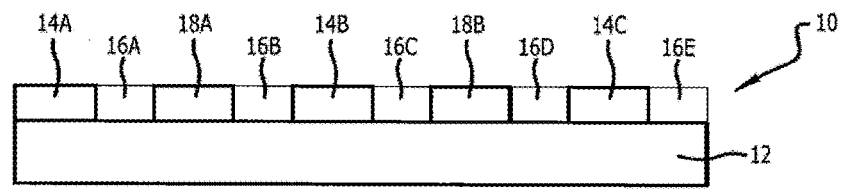
FIG. 3 is an elevation view of an embodiment of a device described herein.
Figure 4:
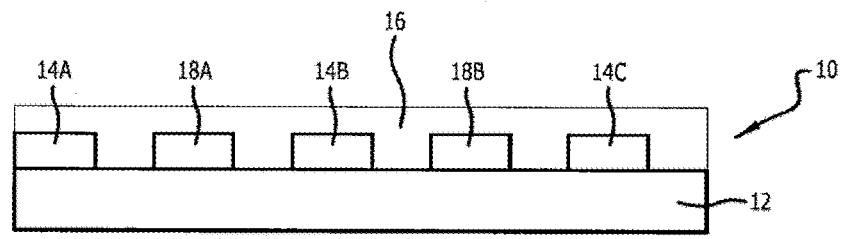
FIG. 4 is an elevation view of an embodiment of a device described herein.

In some embodiments, the sensor element comprises at least an n-type semiconductor material 16. The n-type semiconductor material can comprise any of the aforedescribed doped, loaded and/or physically mixed semiconductors. As shown in FIG. 3, in some embodiments, the n-type semiconductor material, 16A-E, can be disposed between and/or in electrical contact with the first electrode fingers 14A, 14B, and 14C and second electrode fingers 18A and 18B. As shown in FIG. 4, in some embodiments, the n-type semiconductor material 16 can be disposed over the electrodes 14A, 14B, 14C, 18A, and 18B. In some embodiments, the n-type semiconductor material can be disposed over and in between the first and second electrodes.

In some embodiments, the first and second electrodes can be formed from a conductive material. In some embodiments, the conductive material can be gold (Au), platinum (Pt), palladium (Pd) and/or any mixtures thereof.

Figure 5:
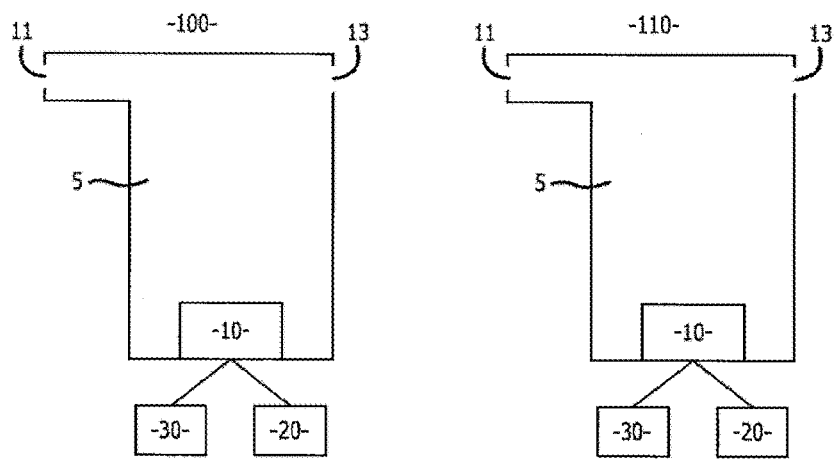
FIG. 5 is a schematic of some embodiments of a gas testing device described herein.

FIG. 5 depicts another embodiment of an sensor system 100 for detecting the presence of constituent gases, e.g., acetone, in a volume of gas. The device may comprise a chamber 5 for containing the volume of gas to be evaluated, and a sensor element 10, disposed therein. In some embodiments, the chamber 5 can comprise a gas inlet 11 for allowing inflow of a gas 9. In some embodiments, the chamber 5 can comprise a gas outlet 13 allowing outflow of gas. In some embodiments, the device can comprise a power supply 20, and a measurement device 30 for analyzing the resistance data received from the gas sensor element, where the measurement device 30 is electrically connected to the sensor element 10 forming an electrical circuit with the first and second electrodes, 14 and 18 (FIGS. 2-4) respectively, such that the resistance across the gas sensor element 10 can be measured.

While not wanting to be limited by theory, it is believed that the presence of the analyte, e.g., acetone, in close proximity to the electrodes and/or semiconductor increases the resistance of the circuit created by 10 between the electrodes 14 and 18, providing a change in the measured resistivity of the circuit. In some embodiments, a measurable correlation between the amount of analyte, e.g., acetone, present in close proximity to the electrodes and the variation in resistance exhibited by the circuit can be effected. In some embodiments, the change in resistivity can be at least about 152 megaohm per 100 part per million (ppm) of analyte present in the tested sampling. The reading is obtained by measuring absolute resistance value and its change directly using computer controlled multi-meter. One method of quantifying rate of sensitivity may include comparing the ascertained sensitivity value of the sensor comprising the co-catalyst to that of a sensor not comprising the co-catalyst. For example, a suitable method of determining the sensitivity value is by the formula: $R_{air}/R_{gas}$ or $R_{gas}/R_{air}$, where $R_{air}$ is the measured resistivity of air (ohms) and $R_{gas}$ is the measured resistivity of the analyte gas, e.g., acetone.

FIG. 5 also depicts an embodiment of a gas sensor system 110 for detecting the presence of multiple gases or a single gas from a mixture of gas. The device may comprise a chamber 5 for containing the volume of gas to be evaluated, and a multi-detector gas sensor element, 20, disposed therein. In some embodiments, the chamber 5 can comprise a gas inlet 11 for allowing inflow of a gas 9. In some embodiments, the chamber 5 can comprise a gas outlet 13 allowing outflow of gas. In some embodiments, the device can comprise a power supply 20, and a measurement device 30 for analyzing the resistivity across the gas sensor element. In some embodiments, such as 110, the measurement device 30 can analyze the individual changes in resistivity across each sensor to determine of the concentration of multiple gas species in a single sample. In some embodiments, the measurement device 30 is electrically connected to the individual sensors' first and second electrodes, 14 and 18 (FIGS. 2-4) respectively, such that there is an individual circuit formed with each sensor so that the resistance across the gas sensor can be measured.

In some embodiments, a method for making a gas sensor composition is described, the method comprising creating an n-type semiconductor precursor aqueous solution an aqueous combustion method. In some embodiments, the gas sensor composition can be used to detect the presence of acetone. In some embodiments, the aqueous combustion method comprises: (1) creating a photocatalytic precursor aqueous solution; (2) heating the solution in a preheated appliance, wherein the preheated appliance has been preheated to substantially near the combustion temperature of the aqueous solution; (3) combustion reacting the precursor solution to create an n-type semiconductor material comprising boron-doped $WO_3$; and then (4) annealing the combustion reaction product.

$WO_3$ compounds, e.g., nanopowders, can be prepared by many different methods including thermal plasma (direct current and including radio frequency inductively-coupled plasma (RF-ICP)), solvothermal, solid state reaction, pyrolysis (spray and flame), and combustion. In some embodiments, the $WO_3$ compounds, e.g., nanopowders, can be prepared by the combustion synthesis methods as described in PCT application PCT/US2013/10201, filed Jan. 4, 2014, which is included herein its entirety by reference, are useful because the high temperature may aid in doping boron into the tungsten oxide lattice and/or may contribute to the stabilization of the epsilon-phase tungsten oxide. Hence, a combustion loading process is a preferred embodiment of the method. In some embodiments, ammonium metatungstate is used as a precursor for $WO_3$. In some embodiments, the additives can further comprise boric acid so that the n-type semiconductor is boron-doped. Preferably, the precursors can be present to about 20 wt % solid in water. In some embodiments, the precursors can also comprise a co-catalyst precursor. In some embodiments, the co-catalyst precursor can comprise $CuO_2$, a precursor for CuO and/or $CeO_2$. In some embodiments, the co-catalyst precursor can comprise $CuO_2$, such that when heated it will be transformed into CuO. The result is a photocatalytic precursor aqueous solution. In some embodiments, the precursors can also include a fuel and an oxidizer. In some embodiments, the precursors can also comprise carbohydrazide and ammonium nitrate as a fuel and an oxidizer respectively. For example, when preparing $WO_3$ nanopowders, a liquid dispersion of additives, e.g., ammonium metatungstate, ammonium nitrate, and/or glycine, in water (5-20 wt % solid in water) can be sprayed into the plasma volume using a two-fluid atomizer. The plasma can be operated at about 25 kW plate power with, for example, argon, nitrogen and/or oxygen gases. The particles formed from the condensed vapor from the plasma can then be collected on filters. In some embodiments, the particle surface areas can range, as measured using Brunauer, Emmett, Teller theory (BET), from about 1 $m^2/g$ to about 500 $m^2/g$, about 15 $m^2/g$ to 30 $m^2/g$, or about 20 $m^2/g$.

In some embodiments, the photocatalytic precursor aqueous solution is then placed in a preheated chamber, wherein the chamber has been preheated to substantially near the combustion temperature of the aqueous solution. In some embodiments, the chamber can be preheated to a temperature ranging between about 100° C. to about 450° C. In some embodiments, the chamber can be preheated to at least about 400° C. In some embodiments, the chamber can be preheated to at least about 420° C. In some embodiments, the combustion temperature is about 420° C. The result is a boron-doped n-type semiconductor. In some embodiments, the precursor solution is then combustion reacted to create a photocatalytic material for duration of between about 10 minutes and about 20 hours. In some embodiments, the combustion reaction is for between about 10 minutes and about 20 hours. In some embodiments, the duration of the combustion can be about 17 hours at about 110° C. In some embodiments, the duration of the combustion can be about 20 minutes at about 420° C. In some embodiments, the duration of the combustion is bounded by when combustion of the materials was substantially complete.

In some embodiments, after combustion reacting, the n-type semiconductor material $WO_3$ is then annealed. In some embodiments, the obtained n-type semiconductor may then be heated from about 200° C. to about 700° C. or about 300° C. to about 500° C. In some embodiments, where there is $CuO_2$ present, the annealing temperature can be at a temperature sufficient to convert substantially all copper metal oxides to CuO. In some embodiments, the annealing temperature is such that at least 95% of all copper metal oxides present are converted to CuO. In some embodiments, the duration of annealing can range from about 15 minutes to 8 hours. In some embodiments, the duration of annealing is more preferably about 2 hours. In some embodiments, the result comprises epsilon-phase $WO_3$. In some embodiments, the result comprises gamma-phased $WO_3$. In some embodiments, the result comprises a mixture of epsilon-phased or gamma-phased $WO_3$. In some embodiments, the result comprises a boron-doped $WO_3$. The result is a gas sensor composition.

Embodiments also include a method for making sensor element. In some embodiments, the gas sensor composition, e.g. boron-doped epsilon-phase or gamma-phase $WO_3$ semiconductor, can be ball milled a time and/or manner sufficient to effect the aforedescribed median size description. The reason for ball milling is to further reduce the semiconductor size population to the aforedescribed ranges, e.g., a median size of about 0.4 μm to about 0.6 μm in diameter. In some embodiments, the aforementioned ranges are achieved by ball milling the gas sensor composition between about 5 hours to about 60 hours. In some embodiments, the composition is more preferably ball milled for about 17 hours. In other embodiments, the composition is more preferably ball milled for about 48 hours. In some embodiments, the aforementioned ranges are achieved by ball milling the gas sensor composition between about 5.00 Hz to about 50.00 Hz, more preferably about 15.00 Hz. In some embodiments, the aforementioned ranges are achieved by ball milling the gas sensor composition, e.g. boron-doped epsilon-phase or gamma-phase WO₃ semiconductor, at about 15.00 Hz for about 17 hours. In some embodiments, where there is a metal oxide co-catalyst present, the metal oxide, e.g. CuO, can comprise plural size populations. In some embodiments, the plural size populations can comprise a metal oxide with a first population with an average diameter of about 3 μm and a second population with an average diameter of about 5 μm. The result is a ball-milled gas sensor composition slurry.

In some embodiments, a gas sensor element can then be created by providing an interdigitated sensor element 10, having the first electrode 14 and second electrode 18 spaced apart. In some embodiments, as shown in FIG. 3 and FIG. 4, the electrodes 14 and 18 are disposed on a substrate 12. In some embodiments, the said ball-milled gas sensor composition slurry, or slurry 16 is deposited between the separated first electrode 14 and second electrode 18, FIG. 3. In some embodiments, the slurry can be drop coated on the electrodes and substrate. In some embodiments, the excess slurry can be removed from the acetone sensor element, so that the remaining n-type semiconductor slurry fills the gap between the electrodes, as in FIG. 4. In other embodiments, the excess slurry is not removed so that a layer is created on top of the electrodes such that the ball-milled gas sensor composition is deposited in a layer 16 on top and between the first and second separated electrodes, FIG. 4. The resulting elements are then dried at a temperature from about 50° C. to 200° C., more preferably about 110° C. for duration of about 15 minutes to about 4 hours, more preferably about 2 hours.

In some embodiments, a multi-detector gas sensor element 20 can be created by affixing to the front and back of an additional or common substrate 12 multiple gas sensor elements 10 with differing material properties, FIG. 1.

In some embodiments, a method for testing for acetone is described, the method comprising: (1) testing a first gas sample at a first temperature with a first sensor, the first sensor comprising a first electrode and a second electrode, wherein the first electrode and the second electrode are separated by a gap of about 1 mil to about 10 mils, and a polycrystalline n-type semiconductor material, wherein the semiconductor material physically contacts both the first and second electrodes and is doped with boron; and (2) testing the same gas sample at a second temperature with a second sensor, wherein the second sensor comprises a first electrode and a second electrode, the first electrode and the second electrode are separated by a gap of about 1 to about 10 mils, and a polycrystalline n-type semiconductor material, wherein the semiconductor material physically contacts both the first and second electrodes and can be doped and/or loaded with Ti, Ce, V, Sm, CuO, and/or a noble metal. In some embodiments, the polycrystalline n-type semiconductor material for the second gas sensor can be also doped with boron. In some embodiments, the polycrystalline n-type semiconductor material for the first gas sensor can be doped and/or loaded with Ti, Ce, V, Sm, CuO, and/or a noble metal. In some embodiments, the noble metal can be selected from Au, Ag, Pt, Pd, Ir, Ru, Rh, or one or more of their oxides, and/or hydroxides. In some embodiments, the noble metal being doped and/or loaded can comprise any combination of palladium, gold and/or platinum. In some embodiments, the polycrystalline n-type semiconductor material can be epsilon-phase WO₃. In some embodiments, the first and second sensors are chosen such that they have different material properties and can exhibit different resistivity reactions in the presence of a mixture of gases. In other embodiments, the first and second sensors have the same material properties but the temperature of the sensors is varied to provide different resistivity reactions. In some embodiments, the first temperature and second temperature can be any temperature within the range from about 0° C. to about 400° C. with the restriction that the first temperature and the second temperatures differ by at least 10° C. In some embodiments, the first temperature is about 350° C. and the second temperature is about 250° C.

In some embodiments of the method described above, the method further comprises comparing the resistivity of each of the first and second sensors to arrive at a determination of the amounts of a first gas and a second gas, where one gas is acetone. In some embodiments of the method described above, one gas detected is acetone and the other gas detected is isoprene. In some embodiments, the method further comprises determining the amounts of acetone and isoprene by using the curve-fit relationships (e.g. power law, hyperbolic, exponential, power, and the like) of the change in resistivity to calculate concentration for each gas based on the first and second gas sensor outputs, where the curve fit relationships are determined by measuring the resistivity of each gas sensor at known concentrations of acetone and isoprene relative to the resistivity of each sensor to air. In some embodiments, the curve-fit relationship can be expressed as a power law fit, as shown in equations 1 and 2:

$$S_H = A\left(C_I + \frac{S_H\left(\frac{1}{B} - \frac{1}{C}\right)}{D}C_A\right)^x \quad [1]$$

$$S_L = E\left(C_I + \frac{S_L\left(\frac{1}{F} - \frac{1}{G}\right)}{H}C_A\right)^y ; \quad [2]$$

where $S_H$ is the sensitivity of the first sensor is at a higher temperature, $S_L$ is the sensitivity of the second sensor at a lower temperature, wherein sensitivity is defined as the resistance measured across the sensor for the gas being measured normalized by the resistance measured across the sensor for air (i.e. $S=R_{gas}/R_{air}$); $C_I$ and $C_A$ are the concentrations of isoprene and acetone respectively in ppm; and the coefficients A, B, C, D, E, F, G, H, x, and y are determined by curve fitting the equation to reflect sensor resistance at known concentrations.

In some embodiments, where the n-type semiconductor is boron-doped WO₃ for both sensors where the sensors are held at different temperatures of about 350° C. and about 250° C., the curve-fit relationship can be expressed as a power law as shown in equations 3 and 4:

$$S_H = 0.219\left(C_I + \frac{S_H\left(\frac{1}{0.404} - \frac{1}{0.462}\right)}{1.46}C_A\right)^{-0.462} \quad [3]$$

-continued $$S_L = 0.157\left(C_I + \frac{S_L\left(\frac{1}{0.289} - \frac{1}{0.459}\right)}{2.04}C_A\right)^{-0.459} \quad [4]$$

where $S_H$ is the sensitivity of the sensor at 350° C., $S_L$ is the sensitivity of the sensor at 250° C., wherein sensitivity is defined as the resistance measured across a sensor for the gas being measured normalized by the resistance measured across that sensor for air, and $C_I$ and $C_A$ are the concentrations of isoprene and acetone respectively in ppm.

In some embodiments, another method for testing for acetone is described, the method comprising: (1) testing a first gas sample at 350° C. with a first gas sensor, the first gas sensor comprising a first electrode and a second electrode, wherein the first electrode and the second electrode are separated by a gap of about 1 mil to about 10 mils, and a polycrystalline n-type semiconductor material, wherein the semiconductor material physically contacts both the first and second electrodes and is doped with boron; and (2) testing the same gas sample at 350° C. with a second gas sensor, wherein the second gas sensor comprises a first electrode and a second electrode, wherein the first electrode and the second electrode are separated by a gap of about 1 to about 10 mils, and a polycrystalline n-type semiconductor material, wherein the semiconductor material physically contacts both the first and second electrodes and is doped and/or loaded with Ti, Ce, V, Sm, CuO, and/or a noble metal. In some embodiments, the polycrystalline n-type semiconductor material for the second gas sensor can be also doped with boron. In some embodiments, the polycrystalline n-type semiconductor material for the first gas sensor can be doped and/or loaded with V, Sm, CuO, and/or a noble metal. In some embodiments, the noble metals can be selected from Au, Ag, Pt, Pd, Ir, Ru, Rh or one or more of their oxides and/or hydroxides. In some embodiments, the noble metal being doped and/or loaded can comprise any combination of palladium, gold and/or platinum. In some embodiments, the polycrystalline n-type semiconductor material can be epsilon-phase $WO_3$. In some embodiments, the first and second gas sensors are chosen such that they have different material properties and can exhibit different reactions in the presence of a mixture of gases. In some embodiments, a method for testing for acetone can be the same as the method described above with the exception that the temperature first sensor and the temperature second sensor can be any temperature within the range from about 0° C. to about 400° C.

In some embodiments of the method described above, the method further comprises comparing the resistivity of each of the first and second sensors to arrive at a determination of the amounts of a first gas and a second gas, where one gas is acetone. In some embodiments of the method described above, one gas detected is acetone and the other gas detected is isoprene. In some embodiments, the method further comprises determining the amounts of acetone and isoprene by using the curve-fit relationships (e.g. power law, hyperbolic, exponential, power, and the like) to calculate concentration for each gas based on the first and second gas sensor outputs, where the curve fit relationships are determined by measuring the resistivity of each gas sensor at known concentrations of acetone and isoprene relative to the resistivity of each sensor to air. In some embodiments, the curve-fit relationship can be expressed as a power law fit, as shown in equations 5 and 6:

$$S_1 = J\left(C_I + \frac{S_1\left(\frac{1}{K} - \frac{1}{L}\right)}{M}C_A\right)^u \quad [5]$$

$$S_2 = N\left(C_I + \frac{S_2\left(\frac{1}{P} - \frac{1}{R}\right)}{S}C_A\right)^v \quad [6]$$

where $S_1$ is the sensitivity of the first sensor, $S_2$ is the sensitivity of the second sensor, wherein sensitivity is defined as the resistance measured across a sensor for the gas being measured normalized by the resistance measured across that sensor for air (i.e. $S=R_{gas}/R_{air}$); $C_I$ and $C_A$ are the concentrations of isoprene and acetone respectively in ppm; and the coefficients J, K, L, M, N, P, R, S, u, and v are determined by curve fitting the equation to reflect each sensor's resistance at known concentrations.

In some embodiments, where the n-type semiconductor for the first sensor is boron-doped $WO_3$ and the n-type semiconductor is Pt-doped, B-doped $WO_3$ for the second sensor where both sensors are held at the same temperature of about 350° C., the curve fit relationship can be expressed as a power law as shown in equations 7 and 8: In some embodiments, where the n-type semiconductor is boron-doped $WO_3$, the curve-fit relationship can be expressed as a power law as shown in equations 7 and 8:

$$S_1 = 0.257\left(C_I + \frac{S_1\left(\frac{1}{0.314} - \frac{1}{0.453}\right)}{0.982}C_A\right)^{-0.453} \quad [7]$$

$$S_2 = 0.710\left(C_I + \frac{S_2\left(\frac{1}{0.531} - \frac{1}{0.158}\right)}{1.25}C_A\right)^{-0.158} \quad [8]$$

where $S_1$ is the sensitivity of the first sensor, $S_2$ is the sensitivity of the second sensor, wherein sensitivity is defined as the resistance measured across a sensor for the gas being measured normalized by the resistance measured across that sensor for air, and $C_I$ and $C_A$ are the concentrations of isoprene and acetone respectively in ppm.

EXAMPLES

It has been discovered that embodiments of the gas sensor elements described herein improve the ability to detect acetone and isoprene. These benefits are further shown by the following examples, which are intended to be illustrative of the embodiments of the disclosure, but are not intended to limit the scope or underlying principles in any way.

Example 1: Making Boron-Doped Epsilon-Phase $WO_3$ (Example 1)

Figure 6:
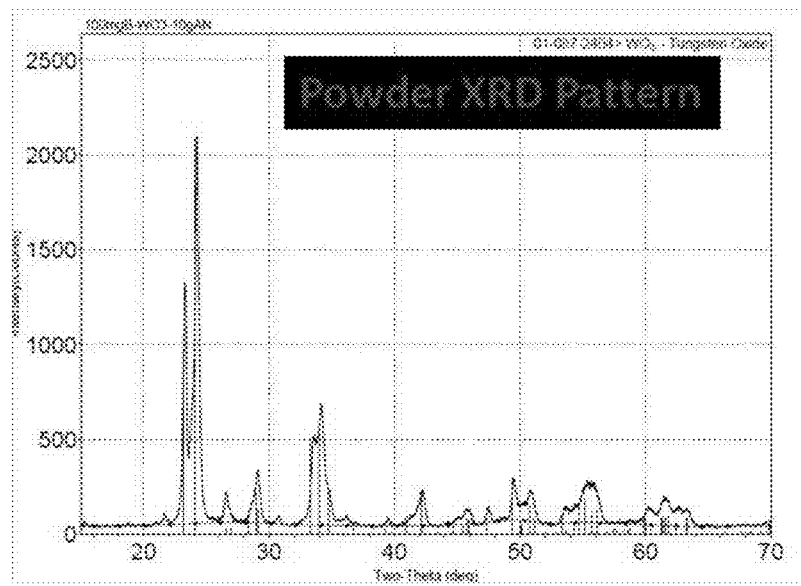
FIG. 6 depicts X-ray diffraction patterns of an embodiment of an n-type semiconductor material described herein, boron-doped $\varepsilon$-$WO_3$.

For Example 1, 5 g of ammonium metatungstate (AMT) hydrate (Sigma Aldrich, St. Louis, Mo., USA), 100 mg boric acid (Aldrich), 2 g carbohydrazide (Aldrich) and 10 g of ammonium nitrate (Aldrich) were dissolved in 50 mL of deionized (DI) water. The aqueous solution was then placed in a muffle furnace, which had been preheated to about 420° C., and then heated for about 20 min or until combustion of the materials was substantially completed. After the combustion of the sample material was completed, the product was annealed in air at about 420° C. for an additional about 20 min. The resulting powder appeared orange-yellow, and was confirmed to be boron-doped $WO_3$ by comparison of the measured XRD pattern (FIG. 6) with a standard ε-$WO_3$ x-ray diffraction (ICFF PDF card number 01-087-2404). The result was 4.6 g of 0.19 wt % ratio boron-doped $WO_3$ or Compound #1, C-1.

TABLE 1

Various N-type Semiconductor Materials Created

| Example | Compound | Comment |
|---------|----------|---------|
| Example 1 | C-1 | B-doped $WO_3$ |
| Example 2 | C-2 | CuO-loaded, B-doped $WO_3$ |
| Example 3 | C-3 | Pt-loaded, B-doped $WO_3$ |
| Example 4 | C-4 | Pt-doped, B-loaded $WO_3$ |
| Example 5 | C-5 | V-doped, B-doped $WO_3$ |
| Example 6 | C-6 | Sm-doped, B-doped $WO_3$ |
| Example 7 | C-7 | V-doped, Pt-doped, B-doped $WO_3$ |
| Example 8 | C-8 | Sm-doped, Pt-doped, B-doped $WO_3$ |

Example 2: CuO Loading of Boron-Doped Epsilon-Phase $WO_3$

For Example 2, 1.0 g of the C-1, made in the manner described above, 27.18 mg of $CuCl_2.2H_2O$ (Aldrich), and 50 mg of urearea (Aldrich) were placed in 10 mL of distilled water and stirred, at a temperature of about 110° C. for about 17 hours in a 40 mL closed vial reactor. The closed vial was then quenched in room temperature tap water and filtered through a membrane filter (0.05 µm pore size), washed with DI water at least three times and finally dried at about 110° C. for about 2 hours. The resulting material was then annealed at about 400° C. in ambient atmosphere and pressure for about 2 hours, resulting in about 4.6 g of 1 wt % ratio CuO-loaded, 0.19 wt % ratio B-doped ε-$WO_3$ or Compound #2, C-2.

Example 3: Noble Metal Loading of Boron-Doped Epsilon-Phase $WO_3$

For Example 3, 1.0 g of the C-1, made in the manner described above, 17.12 g of $Pt(NH_3)_4.(NO_3)_2$ (Aldrich), and 50 mg of urearea (Aldrich) were placed in 10 mL of distilled water and stirred, at a temperature of about 110° C. for about 17 hours in a 40 mL closed vial reactor. The closed vial was then quenched in room temperature tap water and filtered through a membrane filter (0.05 µm pore size), washed with DI water at least three times and finally dried at about 110° C. for about 2 hours. The resulting material was then annealed at about 400° C. in ambient atmosphere and pressure for about 2 hours, resulting in about 4.6 g of 1 wt % ratio Pt-loaded, 0.19 wt % ratio B-doped ε-$WO_3$ or Compound #3, C-3.

Example 4: Noble Metal and Boron-Doped Epsilon-Phase $WO_3$

Figure 7:
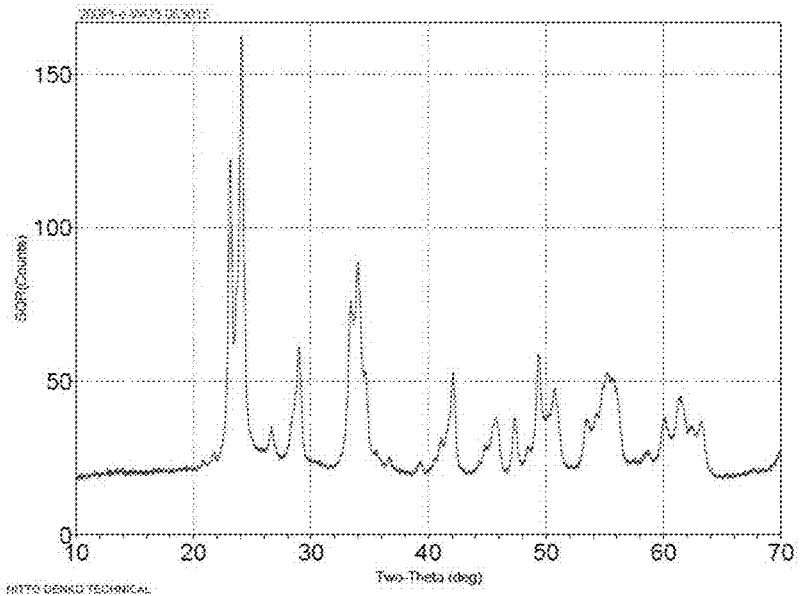
FIG. 7 depicts X-ray diffraction patterns of an embodiment of an n-type semiconductor material described herein, Pt-doped, B-doped $\varepsilon$-$WO_3$.

For Example 4, 5 g of ammonium metatungstate (AMT) hydrate (Aldrich), 100 mg boric acid (Aldrich), 1.826 mg of $Pt(NH_3)_4.(NO_3)_2$ (Aldrich), 2 g carbohydrazide (Aldrich) and 10 g of ammonium nitrate (Aldrich) were dissolved in 50 mL of deionized (DI) water. The aqueous solution was then placed in a muffle furnace, which had been preheated to about 420° C., and then heated for about 20 min or until combustion of the materials was substantially completed. After the combustion of the sample material was completed, the product was annealed in air at about 420° C. for an additional about 20 min. The resultant powder was confirmed to be Pt-doped and boron-doped $WO_3$ by comparison of the measured XRD pattern (FIG. 7) with a standard ε-$WO_3$ x-ray diffraction (ICFF PDF card number 01-087-2404). The result was about 4.6 g of 0.19 wt % ratio boron-doped $WO_3$ or Compound #4, C-4.

Example 5: Vanadium and Boron-Doped Epsilon-Phase $WO_3$ (Prophetic Example)

For Example 5, 5 g of ammonium metatungstate (AMT) hydrate (Aldrich), 100 mg boric acid (Aldrich), 6.995 mg $VC_2O_5$ (EVRAZ Stratcor, Chicago, Ill., USA), 2 g carbohydrazide (Aldrich) and 10 g of ammonium nitrate (Aldrich) can be dissolved in 50 mL of deionized (DI) water. The aqueous solution can then placed in a muffle furnace, which can be preheated to about 420° C., and then heated for about 20 min or until combustion of the materials is substantially completed. After the combustion of the sample material is completed, the product can then be annealed in air at about 420° C. for an additional about 20 min. The result is expected to be 0.02 wt % ratio V-doped and 0.19 wt % ratio boron-doped ε-$WO_3$ or Compound #5, C-5.

Example 6: Samarium and Boron-Doped Epsilon-Phase $WO_3$ (Prophetic Example)

For Example 6, 5 g of ammonium metatungstate (AMT) hydrate (Aldrich), 100 mg boric acid (Aldrich), 6.595 mg of $Sm(NO_3)_3.6H_2O$ (Aldrich), 2 g carbohydrazide (Aldrich) and 10 g of ammonium nitrate (Aldrich) can be dissolved in 50 mL of deionized (DI) water. The aqueous solution can then placed in a muffle furnace, which can be preheated to about 420° C., and then heated for about 20 min or until combustion of the materials is substantially completed. After the combustion of the sample material is completed, the product can then be annealed in air at about 420° C. for an additional about 20 min. The result is expected to be 0.02 wt % ratio Sm-doped and 0.19 wt % ratio boron-doped ε-$WO_3$ or Compound #6, C-6.

Example 7: Vanadium, Platinum, and Boron-Doped Epsilon-Phase $WO_3$

Figure 8:
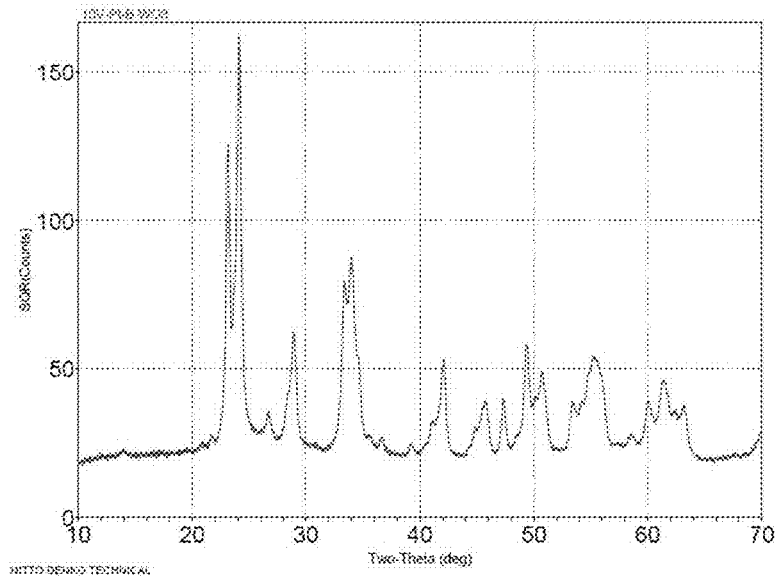
FIG. 8 depicts X-ray diffraction patterns of an embodiment of an n-type semiconductor material described herein, V-doped, Pt-doped, B-doped $\varepsilon$-$WO_3$.

For Example 7, 5 g of ammonium metatungstate (AMT) hydrate (Aldrich), 100 mg boric acid (Aldrich), 6.995 mg of $VC_2O_5$ (EVRAZ Stratcor), 1.826 mg of $Pt(NH_3)_4](NO_3)_2$ (Aldrich), 2 g of carbohydrazide (Aldrich) and 10 g of ammonium nitrate (Aldrich) were dissolved in 50 mL of deionized (DI) water. The aqueous solution was then placed in a muffle furnace, which had been preheated to about 420° C., and then heated for about 20 min or until combustion of the materials was substantially completed. After the combustion of the sample material was completed, the product was annealed in air at about 420° C. for an additional about 20 min. The resultant powder was confirmed to be V-doped, Pt-doped, and boron-doped $WO_3$ by comparison of the measured XRD pattern (FIG. 8) with a standard ε-$WO_3$ x-ray diffraction (ICFF PDF card number 01-087-2404). The result was about 4.6 g 0.02 wt % ratio V-doped, 0.02 wt % ratio Pt-doped, and 0.19 wt % ratio boron-doped ε-$WO_3$ or Compound #7, C-7.

Example 8: Samarium, Platinum, and Boron-Doped Epsilon-Phase $WO_3$

Figure 9:
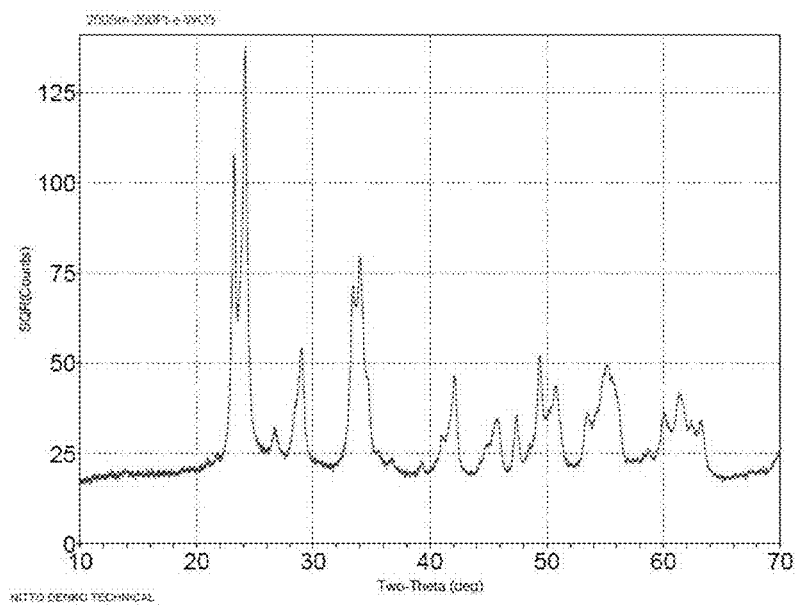
FIG. 9 depicts X-ray diffraction patterns of an embodiment of an n-type semiconductor material described herein, Sm-doped, Pt-doped, B-doped $\varepsilon$-$WO_3$.

For Example 8, 5 g of ammonium metatungstate (AMT) hydrate (Aldrich), 100 mg of boric acid (Aldrich), 6.595 mg of Sm(NO$_3$)$_3$.6H$_2$O (Aldrich), 1.826 mg of Pt(NH$_3$)$_4$] (NO$_3$)$_2$ (Aldrich), 2 g of carbohydrazide (Aldrich) and 10 g of ammonium nitrate (Aldrich) were dissolved in 50 mL of deionized (DI) water. The aqueous solution was then placed in a muffle furnace, which had been preheated to about 420° C., and then heated for about 20 min or until combustion of the materials was substantially completed. After the combustion of the sample material was completed, the product was annealed in air at about 420° C. for an additional about 20 min. The resultant powder was confirmed to be Sm-doped, Pt-doped, and boron-doped WO$_3$ by comparison of the measured XRD pattern (FIG. 9) with a standard ε-WO$_3$ x-ray diffraction (ICFF PDF card number 01-087-2404). The result was about 4.6 g 0.02 wt % ratio Sm-doped, 0.02 wt % ratio Pt-doped, and 0.19 wt % ratio boron-doped ε-WO$_3$ or Compound #8, C-8.

Example 9: Ball-Milled Slurry to Reduce Particle Size

For Example 9, 2.0 g of C-1 and 15.0 mL of methanol (Aldrich) were added to high purity alumina jar to form a solvent-based slurry preparation, and the contents in the jar were then stirred by hand until the mixture seemed liquid-like. Then 20 g of ZrO$_2$ milling media of 3 mm diameter and 4 g of ZrO$_2$ milling media of 5 mm diameter were then added to the alumina jar, and the mixture in the jar was milled by bench-top planetary ball mill (MTI Corporation, Richmond Calif.) for about 17 hours at about 15.00 Hz at room temperature. The resultant mixture was then dried at about 110° C. for about 2 hours in air at room temperature. The result was C-9, or ball milled B-doped WO$_3$.

Particle size distributions of before and after ball milled were attained with a Horiba LA-300 particle size distribution analyzer (Horiba Scientific, Edison, N.J., USA).

For the size determination, 2 g of aqueous sodium pyrophosphate decahydrate (SPD) (Aldrich) was dissolved in about 2 L of reverse osmosis water (RO H$_2$O) to make the SPD solution (0.1 wt % sodium pyrophosphate decahydrate).

Then 2 L of additional RO H$_2$O were circulated and sonicated in the Horiba LA-300 sample chamber for one minute for cleaning ("De-bubble" on). The just circulated and sonicated RO H$_2$O was drained from the sample chamber and the chamber refilled with the SPD solution (Horiba settings at Circulation "8" and "Debubble"). The instrument was blanked (settings at "Init. Alignment", "Alignment", "Blank") and repeated to assure percent total transmission (T %) of the blank was T %=100%.

An initial amount of about 200 mg of ball-milled boron-doped WO$_3$, C-9, was transferred into about 25 mL of the SPD solution and mixed well for about 5 minutes to create a dispersion. The resulting mixture was incrementally loaded into the sample chamber containing SPD solution until the T % dropped to about 75% to about 80%. Upon reaching the desired T %, settings were selected to Circulation "8", sonicating for 10 minutes, and "De-bubble" during the sonication for about 10 min and "R.R. Index" (ratio of refractive index of the solvent") at about 1.654 (i.e. R$_{powder}$/R$_{solvent}$=R$_{WO_3}$/R$_{H_2O}$=(2.22/1.33)=1.654).

Figure 10:
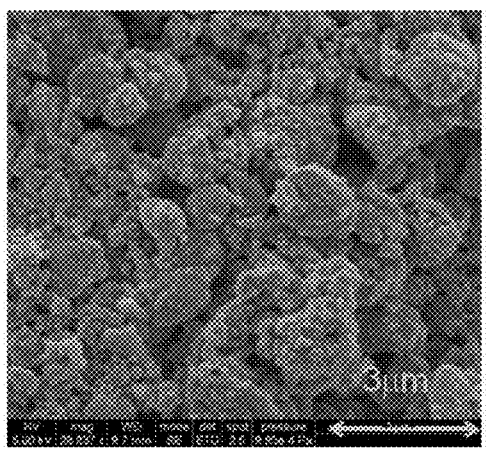
FIG. 10 is a scanning electron microscope image of surfaces comprising the composite element described herein.

A scanning electron micrograph of the resulting ball milled slurry embodiment is shown in FIG. 10. The median diameter for the WO$_3$/0.05% B particles without ball milling was about 13.7233 μm while the median diameter for WO$_3$/0.05% B particles with the ball milling as described above was about 0.5086 μm.

Example 10-16: Ball-Milled Slurry to Reduce Particle Size

Examples 10-16 are ball milled as described in Example 9 using the compositions described in Table 2 below.

TABLE 2

Ball Milling Input and Resultant Compounds.

| Example | Input | Ball Milled Result | Comment |
|---|---|---|---|
| Example 9 | C-1 | C-9 | B-doped WO$_3$ |
| Example 10 | C-2 | C-10 | CuO-loaded, B-doped WO$_3$ |
| Example 11 | C-3 | C-11 | Pt-loaded, B-doped WO$_3$ |
| Example 12 | C-4 | C-12 | Pt-doped, B-loaded WO$_3$ |
| Example 13 | C-5 | C-13 | V-doped, B-doped WO$_3$ (Prophetic) |
| Example 14 | C-6 | C-14 | Sm-doped, B-doped WO$_3$ (Prophetic) |
| Example 15 | C-7 | C-15 | V-doped, Pt-doped, B-doped WO$_3$ |
| Example 16 | C-8 | C-16 | Sm-doped, Pt-doped, B-doped WO$_3$ |

Example 17: Fabrication of a Gas Sensor Element (SE-1)

For Example 17, a gas sensor element was constructed. About 10 mg of ball-milled, boron-doped, epsilon-phase tungsten oxide, C-9, as prepared above, was mixed with 1.0 mL methanol (Aldrich) and sonicated for 60 mins. About seven 10 μl aliquots of the dispersion were dropped onto a sensor element (0.1 inch×0.1 inch electrode, Al$_2$O$_3$ substrate, 10 mils thick, electrode material Au, electrode spacing 4 mils, finger width 4 mils, finger length 0.1 inch and with 3 electrode pairs, P/N 614; Syntechnologies, Colorado, USA), having a surface temperature of about 120° C., and dried between each additional drop. The resulting assembly was then baked on under a full-spectrum Xenon lamp at 300 W output power, for about 60 minutes at about 120° C. The result was a drop coated gas sensor element (SE-1).

TABLE 3

Fabrication of Sensor Elements and Respective Compounds/Properties.

| Example | Input | Sensor Element | Comment |
|---|---|---|---|
| Example 18 | C-9 | SE-1 | Ball-milled B-doped WO$_3$ |
| Example 19 | C-10 | SE-2 | Ball-milled CuO-loaded, B-doped WO$_3$ |
| Example 20 | C-11 | SE-3 | Ball-milled Pt-loaded, B-doped WO$_3$ |
| Example 21 | C-12 | SE-4 | Ball-milled Pt-doped, B-loaded WO$_3$ |
| Example 22 | C-13 | SE-5 | Ball-milled V-doped, B-doped WO$_3$ (Prophetic) |
| Example 23 | C-14 | SE-6 | Ball-milled Sm-doped, B-doped WO$_3$ (Prophetic) |
| Example 24 | C-15 | SE-7 | Ball-milled V-doped, Pt-doped, B-doped WO$_3$ |
| Example 25 | C-16 | SE-8 | Ball-milled Sm-doped, Pt-doped, B-doped WO$_3$ |

Example 18: Fabrication of Gas Sensor Element (SE-2)

Sensor Element 2 (SE-2) was constructed in the same manner as described above for Sensor Element 1 (SE-1) except that instead of using ball-milled, boron-doped, epsilon-phase tungsten oxide C-9, the input was varied to about 10 mg of ball-milled, CuO-loaded, boron-doped, epsilon-phase tungsten oxide C-10, as shown in Table 3. The result was a drop coated gas sensor element (SE-2).

Example 19: Fabrication of Gas Sensor Element (SE-3)

Sensor Element 3 (SE-3) was constructed in the same manner as described above for Sensor Element 1 (SE-1) except that instead of using ball-milled, boron-doped, epsilon-phase tungsten oxide C-9, the input was varied to about 10 mg of ball-milled, Pt-loaded, boron-doped, epsilon-phase tungsten oxide C-11, as shown in Table 3. The result was a drop coated gas sensor element (SE-3).

Example 20: Fabrication of Gas Sensor Element (SE-4)

Sensor Element 4 (SE-4) was constructed in the same manner as described above for Sensor Element 1 (SE-1) except that instead of using ball-milled, boron-doped, epsilon-phase tungsten oxide C-9, the input was varied to about 10 mg of ball-milled, Pt-doped, boron-doped, epsilon-phase tungsten oxide C-12, as shown in Table 3. The result was a drop coated gas sensor element (SE-4).

Example 21: Fabrication of Gas Sensor Element (SE-5) (Prophetic)

Sensor Element 5 (SE-5) will be constructed in the same manner as described above for Sensor Element 1 (SE-1) except that instead of using ball-milled, boron-doped, epsilon-phase tungsten oxide C-9, the input was varied to about 10 mg of ball-milled, V-doped, boron-doped, epsilon-phase tungsten oxide C-13, as shown in Table 3. The result will be a drop coated gas sensor element (SE-5).

Example 22: Fabrication of Gas Sensor Element (SE-6) (Prophetic)

Sensor Element 6 (SE-6) will be constructed in the same manner as described above for Sensor Element 1 (SE-1) except that instead of using ball-milled, boron-doped, epsilon-phase tungsten oxide C-9, the input was varied to about 10 mg of ball-milled, Sm-doped, boron-doped, epsilon-phase tungsten oxide C-14, as shown in Table 3. The result will be a drop coated gas sensor element (SE-6).

Example 23: Fabrication of Gas Sensor Element (SE-7)

Sensor Element 7 (SE-7) was constructed in the same manner as described above for Sensor Element 1 (SE-1) except that instead of using ball-milled, boron-doped, epsilon-phase tungsten oxide C-9, the input was varied to about 10 mg of ball-milled, Pt-doped, V-doped, boron-doped, epsilon-phase tungsten oxide C-15, as shown in Table 3. The result was a drop coated gas sensor element (SE-7).

Example 24: Fabrication of Gas Sensor Element (SE-8)

Sensor Element 8 (SE-8) was constructed in the same manner as described above for Sensor Element 1 (SE-1) except that instead of using ball-milled, boron-doped, epsilon-phase tungsten oxide C-9, the input was varied to about 10 mg of ball-milled, Pt-doped, Sm-doped, boron-doped, epsilon-phase tungsten oxide C-16, as shown in Table 3. The result was a drop coated gas sensor element (SE-8).

Example 25: Single Sensor Gas Sensor Testing [SE-2]

Figure 11:
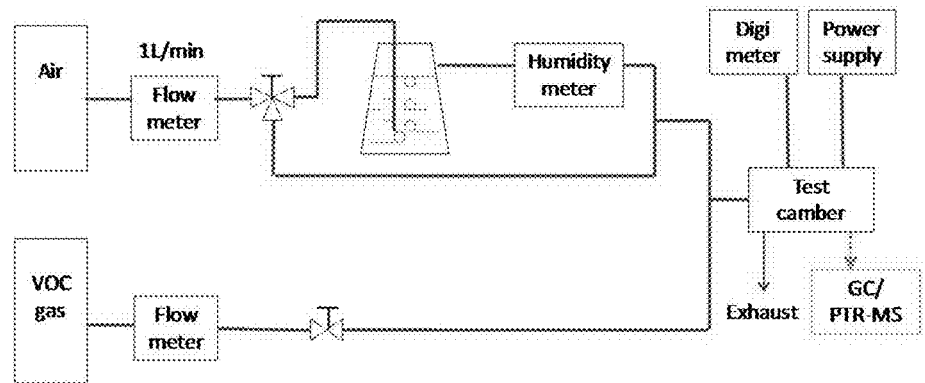
FIG. 11 is a schematic diagram of the testing apparatus used herein.

In Example 25, for single gas sensor element verification, Sensor Element 2, SE-2, (CuO-loaded, B-doped, epsilon-phase $WO_3$) (with heater circuit substrate Synkera P/N 614) constructed as described above was placed in a T-shaped test chamber mimicking the chamber 5 of the embodiment of the gas sensor systems described above and in FIG. 5, with the sensor connected to a multimeter (Tektronix DMM 4050, 6½ Digit Precision Multimeter, Tektronix, Inc., Beaverton, Oreg., USA), set of measure resistivity (ohms) at about 40 kΩ, under ambient atmospheric and in the dark conditions. A diagram of the laboratory setup used to control the inlet airflow to the sensor test chamber is shown in FIG. 11.

The sensor was heated to about 350° C. by applying a voltage of 5.8 volts and a current of 0.162 amps, to resistive heaters to control sensor temperature. Acetone free air (compressed synthetic air [CAS 132259-10-0], Airgas, LLC, San Marcos, Calif., USA) having a relative humidity of greater 90% was then released into the T-tube at about 1.5 L/min to stabilize the baseline resistivity of sensor for about 300 seconds.

Then, concurrently with the 1.5 L/min synthetic air flow (Airgas), 15.1 ppm acetone (Aldrich)/synthetic air (Airgas) mixture was passed at a rate of about 110 mL/min into the system and the resistivity change was monitored at a temperature of about 350° C. for about 150 seconds. The acetone flow was then closed to re-stabilize the sensor back to the base line of resistivity of sensor and flushed with acetone free synthetic air for about 300 seconds.

Ethanol gas (99.4 ppm acetone (Aldrich)/synthetic air (Airgas) mixture at a flow rate of 10 mL/min was then mixed with 1.5 L/min of synthetic air (Airgas) to observe the resistivity change at the temperature of 350° C. for about 150 seconds. The ethanol flow was closed again to stabilize the base line of resistivity of sensor and flushed with ethanol-free synthetic air (Airgas) for about 300 seconds.

Isoprene gas (100.9 ppm isoprene (Aldrich)/synthetic air (Airgas) mixture at a flow rate of 10 mL/min was then mixed with 1.5 L/min of synthetic air (Airgas) to observe the resistivity change at the temperature of 350° C. for about 150 seconds. Isoprene flow was then closed again to stabilize the base line of resistivity of sensor.

The procedure above was repeated for various temperatures including 195° C. where the heater was set at a voltage was 3.8 volts at a current of 0.143 amps.

Figure 14:
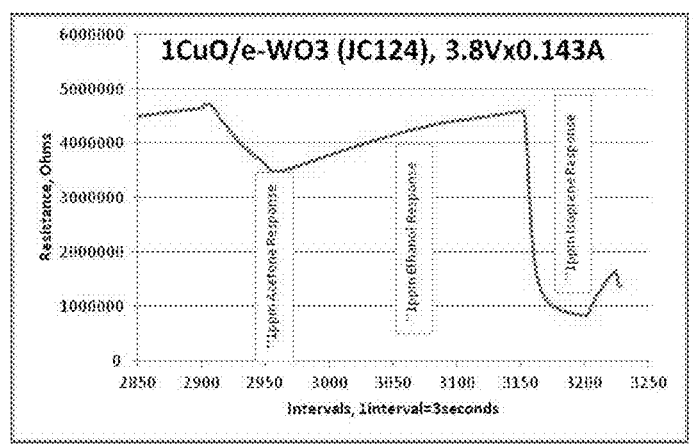
FIG. 14 is a graph depicting the SE-2 sensor sensitivity at 250° C. as described in Example 25.
Figure 15:
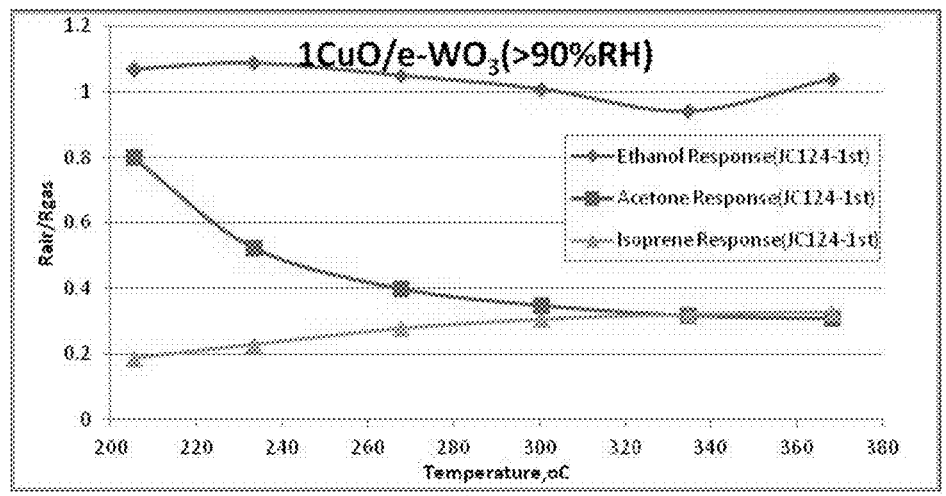
FIG. 15 is a graph depicting the SE-2 sensor sensitivity over various temperatures as described in Example 25.

The changes in resistivity are depicted in FIGS. 13 and 14 for sensor temperatures of 350° C. and 195° C. respectively. The resistivity changes were additionally measured using the same procedure at other various temperatures, ranging from 210° C. to about 360° C. The results of sensor resistivity versus varying temperature are shown in FIG. 15.

Example 26: Multi-Detector Gas Sensor Element Testing [SE-1 and SE-1]

Figure 16:
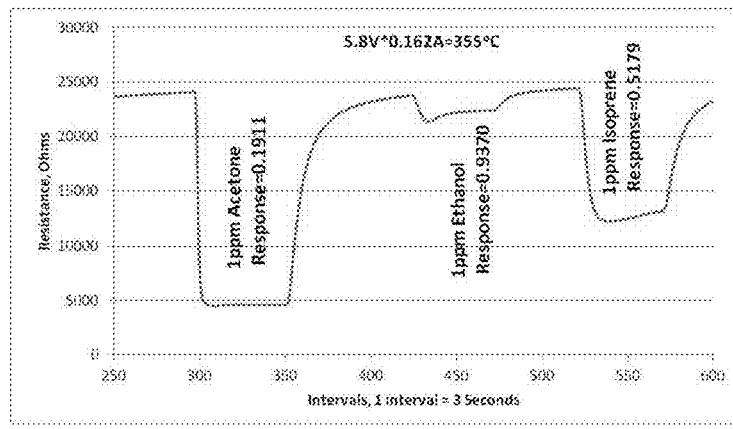
FIG. 16 is a graph depicting the multi-sensor element resistivity response to 1 ppm acetone sample of a SE-2 sensor embodiment at 350° C. as described in Example 26.
Figure 17:
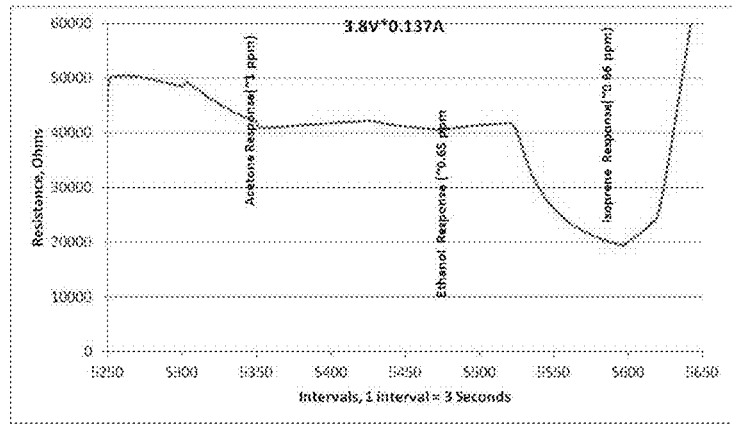
FIG. 17 is a graph depicting the multi-sensor element resistivity response to 1 ppm acetone sample of a SE-2 sensor embodiment at 250° C. as described in Example 26.
Figure 18:
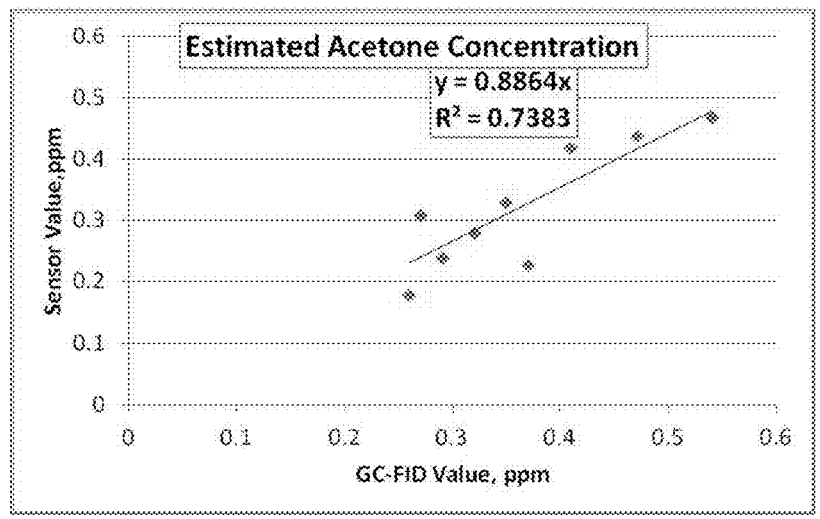
FIG. 18 is a graph depicting the sensor determined acetone concentration as described in Example 26 (using dual SE-1 [boron-doped epsilon phase $WO_3$:B] dual sensor system).
Figure 19:
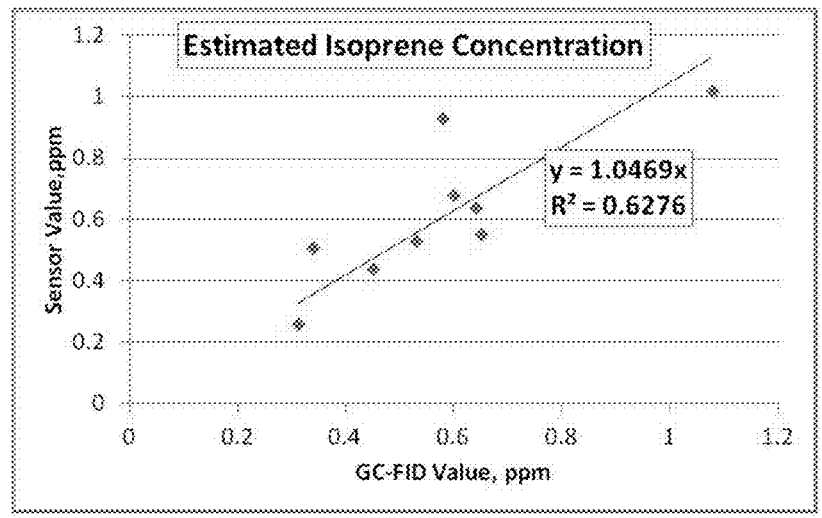
FIG. 19 is a graph depicting the sensor determined isoprene concentration as described in Example 26 (using dual SE-1 dual sensor system).

For Example 26, a multi-detector gas sensor system was constructed and measured as described above in Example 25, except that instead of a single sensor element, two sensor elements were placed in the T-shaped chamber: SE-1 (boron-doped, epsilon-phase $WO_3$) and SE-1 (boron-doped, epsilon-phase $WO_3$) were placed in the apparatus such that there was parallel fluid communication with the individual sensors to yield a multi-detector gas sensor element Dual Sensor #1, similar to the several embodiments shown in FIG. 12. In addition, the sensors were heated using resistive heaters such that the measured temperatures of the sensors were about 350° C. and about 250° C. respectively. Although each sensor is made of the same material, the different temperatures of each sensor would cause them to exhibit a different resistivity response to the same constituent gases. To obtain a sensor temperature of about 350° C., the heater element for the first sensor was set at a voltage of 5.8 V with a current of 0.162 A. To obtain a sensor temperature of about 250° C. the heater element for the second sensor was set at a voltage of 3.8 V with a current of 0.137 A. The dynamic changes in resistivity for each sensor are shown in FIGS. 16 and 17 for 350° C. and 250° C. respectively. The estimated versus measured concentration values for acetone and isoprene are shown in FIGS. 18 and 19 respectively. In addition, the sensor response, e.g. variation in sensitivity, for both acetone and isoprene is shown in FIG. 22 and the sensor prediction for both acetone and isoprene is shown in FIG. 23.

Example 27: Multi-Detector Gas Sensor Element Testing [SE-1 and SE-3]

Figure 20:
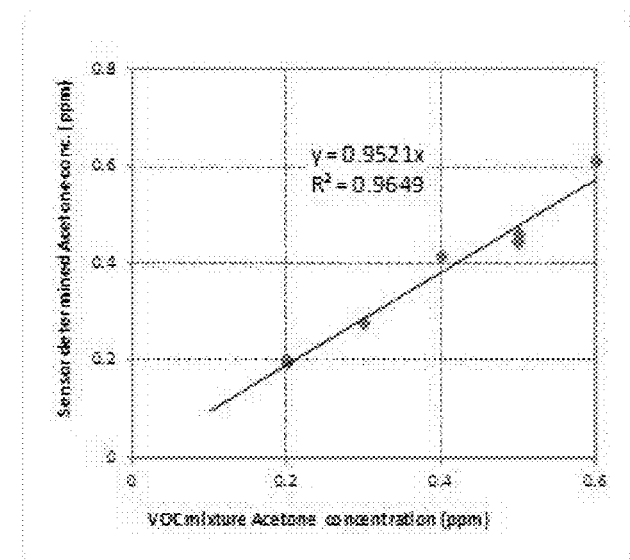
FIG. 20 is a graph depicting the sensor determined acetone concentration as described in Example 27 (using SE-1 [boron-doped epsilon-phase $WO_3$:B] and SE-3 [Pt-loaded, boron-doped epsilon-phase $WO_3$:B] dual sensor system).

A multi-detector gas sensor system was constructed as described above in Example 26, except that sensor element SE-3 (Pt-loaded, boron-doped, epsilon-phase $WO_3$) replaced SE-1 (boron-doped, epsilon-phase $WO_3$). This yielded Dual Sensor #2, a two sensor system with materially different sensors in a configuration similar to the several embodiments are shown in FIG. 12. For the measurement, the procedure was followed as in Example 26 but both sensors were set at about 350° C. The estimated versus measured results are shown in FIGS. 20 and 21 for acetone and isoprene respectively. In addition, the sensor response, e.g. variation in sensitivity, for both acetone and isoprene is shown in FIG. 25.

Example 28: Other Multi-Detector Gas Sensor Element Testing (Prophetic)

A multi-detector gas sensor system can be constructed from any combinations of the sensor elements by placing multi sensor elements in the test chamber and concurrently measuring the resistivity.

Example 29: Determining Curve Fit and Proving Methodology for Detecting Acetone Using a Dual B-Doped $WO_3$ Gas Sensor Element at Different Temperatures In Example 29, Dual Sensor #1 was then taken and measured against known acetone rates such where the first sensor was heated at 5.6 V for a temperature of about 350° C. and the second sensor was heated at 4.6 V for a sensor temperature of about 250° C. and the acetone and isoprene concentration was varied similar to the procedure used in Example 25. The result was that the sensor response was documented for known levels of acetone and isoprene as shown in FIG. 22. As a result, the curve-fit relationships as shown in FIG. 22 were then transformed into a system of equations, Equations 3 and 4, to predict the concentration of acetone and isoprene based on the sensors' resistivity. The result is that the gas sensor element can be used in a method to predict the concentrations of acetone and isoprene from the sensitivity of the high temperature sensor and the sensitivity of the low temperature sensor, wherein sensitivity is defined as the resistance measured across each sensor for the gas being measured normalized by the resistance measured across that sensor for air. Then using the aforementioned relationships, the sensors were then tested against gas samples to validate the method embodiment of using the dual sensor gas sensor element with different temperature sensors to determine the concentration of acetone and isoprene in a gas mixture. The results are shown in FIG. 23, showing an ability to detect the presence of acetone and isoprene.

Example 30: Determining Curve Fit and Proving Methodology for Detecting Acetone Using a Two Different B-Doped $WO_3$ Sensors at the Same Temperature In Example #30, Dual Sensor #2 was then taken and measured against known acetone rates such where both the first and second sensor were heated at 5.6 V for a temperature of about 350° C. and the acetone and isoprene concentration was varied similar to the procedure used in Example 25. The result was that the sensor response was documented for known levels of acetone and isoprene as shown in FIG. 24. As a result, the curve-fit relationships shown in FIG. 24 were then used to form a system of equations, Equations 7 and 8, to predict the level of acetone and isoprene based on the sensor's resistivity. The result is that the sensor can be used in a method to predict the concentrations of acetone and isoprene from the sensitivities of the two different sensors, wherein sensitivity is defined as the resistance measured across each sensor for the gas being measured normalized by the resistance measured across that sensor for air. Then using the aforementioned relationships, the sensors were then tested against gas samples to validate the method embodiment of using the dual sensor gas sensor element with different material sensors to determine the concentration of acetone and isoprene in a gas mixture. The results are shown in FIG. 25, showing an ability to detect the presence of acetone and isoprene.

Embodiments

The following embodiments are contemplated as a non-limiting list of applications of the subject matter of the present disclosure.
1. A gas sensor element comprising a first sensor comprising:
   a first electrode, a second electrode, and a first polycrystalline n-type semiconductor material;
   wherein the first electrode and the second electrode are separated by a gap of about 1 mil to about 10 mils; and
   wherein the first polycrystalline n-type semiconductor material comprises boron-doped $WO_3$ that is optionally doped or loaded with V, Sm, CuO, or a combination thereof; and
   the first polycrystalline n-type semiconductor material is in physical contact with both the first and second electrodes.
2. A gas sensor element of embodiment 1, further comprising a second sensor comprising:
   a third electrode, a fourth electrode, and a second polycrystalline n-type semiconductor material;
   wherein the third electrode and the fourth electrode are separated by a gap of about 1 mil to about 10 mils;
   wherein the second polycrystalline n-type semiconductor material comprises boron-doped $WO_3$; and wherein the second polycrystalline n-type semiconductor material is in physical contact with both the third electron and the fourth electrode.

3A. The gas sensor element of embodiment 2, wherein the first polycrystalline n-type semiconductor material has a different chemical composition than the second polycrystalline n-type semiconductor material.

3. The gas sensor element of embodiment 1, wherein the first polycrystalline n-type semiconductor material is doped or loaded with V, Sm, or a combination thereof.

4. The gas sensor element of embodiment 1, wherein the first polycrystalline n-type semiconductor material is further doped or loaded with a noble metal.

5. The gas sensor element of embodiment 2, wherein the second polycrystalline n-type semiconductor material is further doped or loaded with a noble metal.

6. The gas sensor element of embodiment 4, wherein the noble metal is palladium, gold, platinum, or a combination thereof.

7. The gas sensor element of embodiment 5, wherein the noble metal is palladium, gold, platinum, or a combination thereof.

7A. The gas sensor element of embodiment 6 or 7, wherein the noble metal is platinum.

8. The gas sensor element of embodiment 2, wherein second polycrystalline n-type semiconductor material is further doped or loaded with V, Sm, CuO, or a combination thereof.

9. The gas sensor element of embodiment 1, wherein the first polycrystalline n-type semiconductor material is further doped with Ti, Ce, or a combination thereof.

10. The gas sensor element of embodiment 2, wherein the second polycrystalline n-type semiconductor material is further doped with Ti, Ce, or a combination thereof.

11. The gas sensor element of embodiment 1, wherein the $WO_3$ is epsilon-phase $WO_3$.

12. The gas sensor element of embodiment 2, wherein the $WO_3$ is epsilon-phase $WO_3$.

13. A method for testing for the presence of acetone comprising:
   (a) testing a gas sample at 350° C. with a first sensor, wherein the first sensor comprises:
      a first electrode, a second electrode, and a first polycrystalline n-type semiconductor material;
      wherein the first electrode and the second electrode are separated by a gap of about 1 mil to about 10 mils; and
      wherein the first polycrystalline n-type semiconductor material comprises boron-doped $WO_3$ that is doped or loaded with Ti, Ce, V, Sm, CuO, or a combination thereof; and
      the first polycrystalline n-type semiconductor material is in physical contact with both the first electrode and the second electrode,
   (b) testing the same gas sample at 250° C. with a second sensor, wherein the second sensor comprises:
      a third electrode, a fourth electrode, and a second polycrystalline n-type semiconductor material;
      wherein the third electrode and the fourth electrode are separated by a gap of about 1 mil to about 10 mils;
      wherein the second polycrystalline n-type semiconductor material comprises $WO_3$, and is optionally doped or loaded with Ti, Ce, V, Sm, CuO, a noble metal, or a combination thereof; and
      wherein the second polycrystalline n-type semiconductor material is in physical contact with both the third electron and the fourth electrode, and
   (c) comparing the resistivity of each of the first and second sensors to arrive at a determination of the amounts of acetone and a second gas.

14. The method of embodiment 13, where the second polycrystalline n-type semiconductor material is further doped with boron.

15. The method of embodiment 13, where the first polycrystalline n-type semiconductor material is doped or loaded with V, Sm, CuO, a noble metal, or a combination thereof.

16. The method of embodiment 15, wherein the noble metal is palladium, gold, platinum, or a combination thereof.

17. The method of embodiment 13, wherein the $WO_3$ is epsilon-phase $WO_3$.

18. The method of embodiment 13, wherein the one gas detected is acetone and the other gas detected is isoprene.

19. A method for testing for the presence of acetone comprising:
   (a) testing a gas sample at 350° C. with a first sensor, wherein the first sensor comprises:
      a first electrode, a second electrode, and a first polycrystalline n-type semiconductor material;
      wherein the first electrode and the second electrode are separated by a gap of about 1 mil to about 10 mils; and
      wherein the first polycrystalline n-type semiconductor material comprises boron-doped $WO_3$ that is doped or loaded with Ti, Ce, V, Sm, CuO, or a combination thereof; and
      the first polycrystalline n-type semiconductor material is in physical contact with both the first electrode and the second electrode,
   (b) testing the same gas sample at 350° C. with a second sensor, wherein the second sensor comprises:
      a third electrode, a fourth electrode, and a second polycrystalline n-type semiconductor material;
      wherein the third electrode and the fourth electrode are separated by a gap of about 1 mil to about 10 mils;
      wherein the second polycrystalline n-type semiconductor material comprises $WO_3$, and is doped or loaded with Ti, Ce, V, Sm, CuO, a noble metal, or a combination thereof, such that the material properties between the first sensor and the second sensor differ; and
      wherein the second polycrystalline n-type semiconductor material is in physical contact with both the third electron and the fourth electrode, and
   (c) comparing the resistivity of each of the first and second sensors to arrive at a determination of the amounts of acetone and a second gas.

20. The method of embodiment 19, where the second polycrystalline n-type semiconductor material is further doped with boron.

21. The method of embodiment 19, where the first polycrystalline n-type semiconductor material is doped or loaded with V, Sm, CuO, a noble metal, or a combination thereof.

22. The method of embodiment 21, wherein the noble metal is palladium, gold, platinum, or a combination thereof.

23. The method of embodiment 19, wherein the WO$_3$ is epsilon-phase WO$_3$.

24. The method of embodiment 19, wherein the one of the first gas and the second gas is acetone and the other of the first gas and the second gas is isoprene.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A gas sensor element comprising a first sensor comprising:
a first electrode, a second electrode, and a first polycrystalline n-type semiconductor material; wherein the first electrode and the second electrode are separated by a gap of about 1 mil to about 10 mils; and wherein the first polycrystalline n-type semiconductor material comprises boron-doped WO$_3$ that is doped or loaded with Pt, V, Sm, CuO, or a combination thereof; and the first polycrystalline n-type semiconductor material is in physical contact with both the first electrode and the second electrode.

2. A gas sensor element of claim 1, further comprising:
a second sensor comprising: a third electrode, a fourth electrode, and a second polycrystalline n-type semiconductor material; wherein the third electrode and the fourth electrode are separated by a gap of about 1 mil to about 10 mils; wherein the second polycrystalline n-type semiconductor material comprises boron-doped WO$_3$; and wherein the second polycrystalline n-type semiconductor material is in physical contact with both the third electrode and the fourth electrode.

3. The gas sensor element of claim 2, wherein the second polycrystalline n-type semiconductor material is further doped or loaded with a noble metal.

4. The gas sensor element of claim 3, wherein the noble metal is palladium, gold, platinum, or a combination thereof.

5. The gas sensor element of claim 2, wherein the second polycrystalline n-type semiconductor material is further doped or loaded with V, Sm, CuO, or a combination thereof.

6. The gas sensor element of claim 2, wherein the second polycrystalline n-type semiconductor material is further doped with Ti, Ce, or a combination thereof.

7. The gas sensor element of claim 2, wherein the WO$_3$ of the first and second polycrystalline n-type semiconductor material is epsilon-phase WO$_3$.

8. The gas sensor element of claim 1, wherein the first polycrystalline n-type semiconductor material is doped or loaded with V, Sm, or a combination thereof.

9. The gas sensor element of claim 1, wherein the first polycrystalline n-type semiconductor material is further doped or loaded with a noble metal other than Pt.

10. The gas sensor element of claim 9, wherein the noble metal is palladium, gold, or a combination thereof.

11. The gas sensor element of claim 1, wherein the first polycrystalline n-type semiconductor material is further doped with Ti, Ce, or a combination thereof.

12. The gas sensor element of claim 1, wherein the WO$_3$ is epsilon-phase WO$_3$.

* * * * *